United States Patent [19]

Okamoto et al.

[11] Patent Number: 4,670,420

[45] Date of Patent: * Jun. 2, 1987

[54] N²-DANSYL-L-ARGININE DERIVATIVES, AND THE PHARMACEUTICALLY ACCEPTABLE ACID ADDITION SALTS THEREOF

[75] Inventors: Shosuke Okamoto, Hyogo; Ryoji Kikumoto, Tokyo; Yoshikuni Tamao, Kanagawa; Shinji Tonomura; Kazuo Ohkubo, both of Tokyo, all of Japan

[73] Assignees: Mitsubishi Chemical Industries Limited, Tokyo; Shosuke Okamoto, Kobe, both of Japan

[*] Notice: The portion of the term of this patent subsequent to Sep. 6, 1994 has been disclaimed.

[21] Appl. No.: 118,096

[22] Filed: Feb. 4, 1980

Related U.S. Application Data

[60] Continuation of Ser. No. 691,766, Jun. 1, 1976, Pat. No. 4,227,006, which is a division of Ser. No. 496,939, Aug. 13, 1974, Pat. No. 3,978,045.

[30] Foreign Application Priority Data

| Aug. 13, 1973 | [JP] | Japan | 48-090699 |
|---|---|---|---|
| Oct. 16, 1973 | [JP] | Japan | 48-116035 |
| Oct. 18, 1973 | [JP] | Japan | 48-117292 |
| Dec. 10, 1973 | [JP] | Japan | 48-137501 |
| Mar. 19, 1974 | [JP] | Japan | 49-031141 |
| Mar. 25, 1974 | [JP] | Japan | 49-033260 |
| May 31, 1974 | [JP] | Japan | 49-061573 |

[51] Int. Cl.⁴ .................... C07C 143/80; A61K 37/02
[52] U.S. Cl. .................................. 514/20; 560/10
[58] Field of Search .............. 260/112.5 R; 560/10; 424/309, 177; 514/20

[56] References Cited

U.S. PATENT DOCUMENTS

| 4,069,317 | 1/1978 | Okamoto | 260/112.5 R |
| 4,069,329 | 1/1978 | Okamoto | 560/10 |
| 4,072,743 | 2/1978 | Okamoto | 260/112.5 R |
| 4,072,744 | 2/1978 | Okamoto | 260/112.5 R |
| 4,227,006 | 10/1980 | Okamoto | 560/10 |

OTHER PUBLICATIONS

Wilson, "Textbook of Organic Medical and Pharmaceutical Chemistry," pp. 39, 40 & 50 (1954).

Primary Examiner—Michael L. Shippen
Attorney, Agent, or Firm—Oblon, Fisher, Spivak, McClelland & Maier

[57] ABSTRACT

N²-dansyl-L-arginine esters and amides having the formula

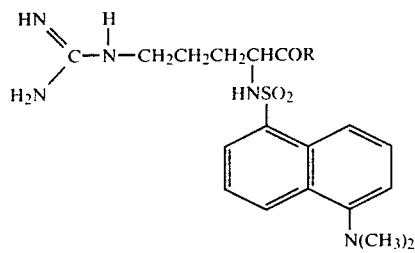

or the acid addition salts thereof with a pharmaceutically acceptable acid, wherein R is selected from the group consisting of (1) alkoxy, alkenyloxy, alkynyloxy, and cycloalkoxy, respectively, containing not more than 10 carbon atoms, aralkyl of not more than 15 carbon atoms, tetrahydrofurfuryloxy, and alkoxy of not more than 10 carbon atoms substituted with an alkoxy group of not more than 10 carbon atoms, halogen or nitro; (2)

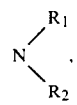

wherein $R_1$ and $R_2$ are members selected from the group consisting of hydrogen, alkyl, aryl, aralkyl, cycloalkyl, cycloalkylalkyl, alkenyl, and alkyl, wherein said member has no more than 10 carbon atoms, and wherein said alkyl may be substituted with a member selected from the group consisting of alkoxy, alkoxycarbonyl, arylcarbamoyl, acyl, acyloxy, N,N-polymethylenecarbamoyl, respectively, containing not more than 10 carbon atoms, and carboxyl; and (2)

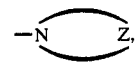

wherein Z is a divalent group containing up to 10 carbon atoms, which consists of more than one group selected from the group consisting of methylene —CH₂, monosubstituted methylene

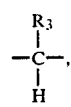

wherein $R_3$ is selected from the group consisting of alkyl, acyl, alkoxy, and alkoxycarbonyl, respectively, containing not more than 10 carbon atoms, and carbamoyl, and disubstituted methylene

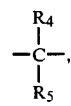

wherein R₄ R₅ are alkyl groups of not more than 10 carbon atoms, and which may further contain at least one member selected from the group consisting of oxy —O—, thio —S—, cycloalkylene of not more than 10 carbon atoms, imino

alkyl substituted imino

wherein R₆ is an alkyl group of not more than 10 carbon atoms, acyl substituted imino

wherein R₇ is an alkyl group of not more than 10 carbon atoms, phenylene

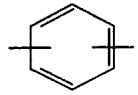

and carbonyl

which completes the

ring together with the said methylene, mono-substituted methylene or disubstituted methylene.

6 Claims, No Drawings

$N^2$-DANSYL-L-ARGININE DERIVATIVES, AND THE PHARMACEUTICALLY ACCEPTABLE ACID ADDITION SALTS THEREOF

This is a continuation of application Ser. No. 691,766, filed June 1, 1976, now U.S. Pat. No. 4,227,006, which is a division of application Ser. No. 496,939, filed Aug. 13, 1974, now U.S. Pat. No. 3,978,045.

BACKGROUND OF THE INVENTION

1. Field of the Invention

This invention relates to certain new and useful $N^2$-dansyl-L-arginine esters and amides, and the pharmaceutically acceptable acid addition salts thereof, which are of especial value in view of their outstanding antithrombotic properties.

2. Description of the Prior Art

In the past, there have been many attempts to obtain new and improved agents for the treatment of thrombosis. Of these, $N^2$-(p-tolylsulfonyl)-L-arginine esters are known to be effective in dissolving blood clots. (U.S. Pat. No. 3,622,615, patented Nov. 23, 1971). A need continues to exist however, for a highly specific inhibitor on thrombin for the control of thrombosis.

SUMMARY OF THE INVENTION

Accordingly, one object of the present invention is to provide a group of $N^2$-dansyl-L-arginine esters, amides and pharmaceutically acceptable acid addition salts.

Another object of the present invention is to provide a group of $N^2$-dansyl-L-arginine esters, amides and pharmaceutically acceptable acid addition salts which are useful in the diagnostic selective determination of thrombin in blood and in drug therapy as antithrombotic agents.

Briefly, these objects and other objects of the present invention as hereinafter will become more readily apparent can be attained by $N^2$-dansyl-L-arginine esters and amides of formula (I):

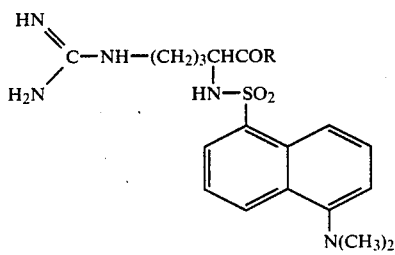

or the acid addition salts thereof with a pharmaceutically acceptable acid, wherein R is selected from the group consisting of (1) alkoxy, alkenyloxy, alkynyloxy, and cycloalkoxy, respectively, containing not more than 10 carbon atoms, aralkyl or not more than 15 carbon atoms, tetrahydrofurfuryloxy, and alkoxy of not more than 10 carbon atoms substituted with an alkoxy group of not more than 10 carbon atoms, halogen or nitro; (2)

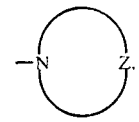

wherein $R_1$ and $R_2$ are members selected from the group consisting of hydrogen, alkyl, aryl, aralkyl, cycloalkyl, cycloalkylalkyl, alkenyl, and alkyl, wherein said member has no more than 10 carbon atoms, and wherein said alkyl may be substituted with a member selected from the group consisting of alkoxy, alkoxycarbonyl, arylcarbamoyl, acyl, acyloxy, N,N-polymethylenecarbamoyl, respectively, containing not more than 10 carbon atoms, and carboxyl; and (2)

wherein Z is a divalent group containing up to 10 carbon atoms, which consists of more than one group selected from the group consisting of methylene —$CH_2$, monosubstituted methylene

wherein $R_3$ is selected from the group consisting of alkyl, acyl, alkoxy, and alkoxycarbonyl, respectively, containing not more than 10 carbon atoms, and carbamoyl, and disubstituted methylene

wherein $R_4$ and $R_5$ are alkyl groups of not more than 10 carbon atoms, and which may further contain at least one member selected from the group consisting of oxy—O—, thio—S—, cycloalkylene of not more than 10 carbon atoms, imino

alkyl substituted imino

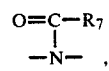

wherein $R_6$ is an alkyl group of not more than 10 carbon atoms, acyl substituted imino

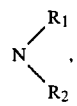

wherein $R_7$ is an alkyl group of not more than 10 carbon atoms, phenylene

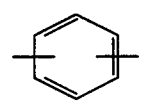

and carbonyl

which completes the

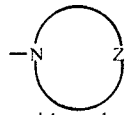

ring together with the said methylene, monosubstituted methylele or disubstituted methylene.

DETAILED DESCRIPTION OF THE PREFERRED EMBODIMENTS

In the formula (I), R is preferably alkoxy of 1–8 carbon atoms, aralkyloxy of 7–9 carbon atoms, alkenyloxy of 3–6 carbon atoms, alkynyloxy of 3–6 carbon atoms, cyclohexyloxy, tetrahydrofurfuryloxy, ω-alkoxyalkyloxy of 2–6 carbon atoms, ω-chloroalkyloxy of 2–6 carbon atoms, 2-nitrobutyloxy, alkylamino of 1–9 carbon atoms, ω-alkoxyalkylamino of 2–6 carbon atoms, ω-alkoxycarbonyl-alkylamino of 2–8 carbon atoms, alkenylamino of 3–5 carbon atoms, cyclopropylamino, cyclohexylmethylamino, phenylamino, aralkylamino of 7–10 carbon atoms, 2-phenylcarbamoylethylamino, N,N-tetramethylenecarbamoylmethylamino, dialkylamino of 2–10 carbon atoms, N-alkyl-N-(ω-alkoxycarbonylalkyl)amino of 3–7 carbon atoms, N-alkyl-N-aralkylamino of 8–10 carbon atoms, N-alkyl-N-(ω-acylalkyl)amino of 4–8 carbon atoms, N,N-polymethyleneiminyl of 3–10 carbon atoms, N,N-polymethyleneiminyl of 3–10 carbon atoms substituted with alkyl of 1–5 carbon atoms, alkoxycarbonyl of 2–5 carbon atoms, acyl of 2–5 carbon atoms, and carbamoyl; n-(tetrahydro-1,n-oxazinyl), wherein n is the integers 2, 3 or 4, n-(tetrahydro-1,n-oxyazinyl), wherein n is the integers 2, 3 or 4 and which is substituted by one or two alkyl groups of 1–5 carbon atoms; 2-isoindolinyl, 4-alkyl-1-piperazinyl of 5–8 carbon atoms, 1,2,3,4-tetrahydro-1-quinolyl, and 4-(4-azabicyclo(3.2.2)nonyl).

Suitable compounds of this invention include $N^2$-dansyl-L-arginine esters and amides such as $N^2$-dansyl-L-arginine ethyl ester, $N^2$-dansyl-L-arginine n-propyl ester, $N^2$-dansyl-L-arginine n-butyl ester, $N^2$-dansyl-L-arginine n-amyl ester, $N^2$-dansyl-L-arginine isopentyl ester, $N^2$-dansyl-L-arginine n-hexyl ester, $N^2$-dansyl-L-arginine benzyl ester, $N^2$-dansyl-L-arginine crotyl ester, $N^2$-dansyl-L-arginine 3-butynyl ester, $N^2$-dansyl-L-arginine 2-methoxyethyl ester, $N^2$-dansyl-L-arginine 3-chloropropyl ester, $N^2$-dansyl-L-arginine 4-chlorobutyl ester, $N^2$-dansyl-N-(n-butyl)-L-argininamide, $N^2$-dansyl-N-(2-methoxyethyl)-L-argininamide, $N^2$-dansyl-N-(2-ethoxyethyl)-L-argininamide, $N^2$-dansyl-N-(2-methoxycarbonylethyl)-L-argininamide, $N^2$-dansyl-N-(2-ethoxycarbonylethyl)-L-argininamide, $N^2$-dansyl-N-allyl-L-argininamide, $N^2$-dansyl-N-methyl-N-(n-butyl)-L-argininamide, $N^2$-dansyl-N-methyl-N-(2-methoxycarbonylethyl)-L-argininamide, $N^2$-dansyl-N-methyl-N-benzyl-L-argininamide, $N^2$-dansyl-N-methyl-N-(2-acetylethyl)-L-argininamide, 1-($N^2$-dansyl-L-arginyl)-pyrrolidine, 1-($N^2$-dansyl-L-arginyl)piperidine, 2-methyl-1-($N^2$-dansyl-L-arginyl)piperidine, 3-methyl-1-($N^2$-dansyl-L-arginyl)piperidine, 4-methyl-1-($N^2$-dansyl-L-arginyl)piperidine, 4-ethyl-1-($N^2$-dansyl-L-arginyl)piperidine, 4-(n-propyl)-1-($N^2$-dansyl-L-arginyl)piperidine, 4-(isopropyl)-1-($N^2$-dansyl-L-arginyl)piperidine, 4-methoxycarbonyl-1-($N^2$-dansyl-L-arginyl)piperidine, 4-acetyl-1-($N^2$-dansyl-L-arginyl)piperidine, $N^2$-dansyl-N,N-hexamethylene-L-argininamide, $N^2$-dansyl-N,N-heptamethylene-L-argininamide, $N^2$-dansyl-N,N-octamethylene-L-argininamide, 4-($N^2$-dansyl-L-arginyl)morpholine, 2-($N^2$-dansyl-L-arginyl)isoindoline, 4-methyl-1-($N^2$-dansyl-L-arginyl)piperazine, and $N^2$-dansyl-N-(1,2,3,4-tetrahydro-1-quinolyl)argininamide.

These particular compounds are highly potent in their antithrombotic activity.

For the preparation of the compounds of this invention, various methods can be employed depending upon the particular starting materials and/or intermediates involved. Successful preparation of these compounds is possible by way of several synthetic routes which are outlined below.

(1) Preparation of $N^2$-dansyl-L-arginine esters $N^2$-dansyl-L-arginine, which is the starting material for the preparation of $N^2$-dansyl-L-arginine esters, is most generally obtained by reacting L-arginine and dansyl chloride, that is, 5-dimethylamino-1-naphthalenesulfonyl chloride, in the presence of a base. However, $N^2$-dansyl-L-arginine may also be obtained by reacting ornithine, the ω-position of which is protected, with dansyl chloride in the presence of a base, removing the protective group at the ω-position of the product, and thereafter guanidylating the obtained $N^2$-dansyl ornithine by conventional procedures.

$N^2$-dansyl-L-arginine esters or acid addition salts thereof are prepared by esterifying the above-mentioned $N^2$-dansyl-L-arginine in accordance with the processes explained below.

(a) Esterification of $N^2$-dansyl-L-arginine with an alcohol (i) Esterification by heating $N^2$-dansyl-L-arginine and an alcohol The reaction rate is low in this method which is therefore conducted under high pressure at an elevated temperature. Care must be exercised, since $N^2$-dansyl-L-arginine is easily decomposed at high temperatures.

(ii) Esterification of $N^2$-dansyl-L-arginine with an alcohol in the presence of an esterification catalyst Suitable esterification catalysts include hydrogen halides, such as hydrogen chloride, hydrogen bromide or the like; mineral acids such as sulfuric acid, nitric acid, phosphoric acid, or the like; organic acids, such as toluenesulfonic acid, benzenesulfonic acid, methanesulfonic acid, trifluoromethanesulfonic acid, trifluoroacetic acid, cationic ion exchange resins or the like; and Lewis acids, such as boron trifluoride, aluminum chloride, or the like. Strong acids are especially suitable.

A strong acid esterification catalyst adds to an $N^2$-dansyl-L-arginine ester to form an acid addition salt thereof. Normally, 2 equivalents of acid add to 1 equivalent of $N^2$-dansyl-L-arginine ester, and therefore, 2 equivalents or more of the esterification catalyst are preferably used for each 1 equivalent of $N^2$-dansyl-L-arginine.

Suitable alcohols for the above-mentioned esterification include primary, secondary, and tertiary alkyl alcohols containing up to 10 carbon atoms, such as methanol, ethanol, n-propanol, isopropyl alcohol, tert-butyl alcohol, n-amyl alcohol, n-hexyl alcohol, 2-ethylhexanol; aralkyl alcohols containing up to 15 carbon atoms, such as benzyl alcohol, phenethyl alcohol, 1-phenylethanol, 1-phenyl-1-propanol, or the like; tetrahydrofurfuryl alcohol; alkenyl alcohols containing up to 10 carbon atoms, such as allyl alcohol, crotyl alcohol, methyl vinyl carbinol, or the like; alkynyl alcohols containing up to 10 carbon atoms, such as propargyl alcohols, 3-butyn-1-ol, or the like; cycloalkyl alcohols containing up to 10 carbon atoms, such as cyclohexanol, cyclopentanol, or the like; and alkyl alcohols containing up to 10 carbon atoms substituted by an alkoxy group of up to 10 carbon atoms, a halogen or a nitro group, such as 3-chloro-1-propanol, 2-chloro-1-propanol, 1-chloro-2-propanol, 2-fluoro-1-ethanol, 2-chloro-1-ethanol, 4-chloro-1-butanol, 2-nitro-1-butanol, 3-nitro-1-propanol, 2-methoxyethanol, 3-ethoxypropanol, or the like.

$N^2$-dansyl-L-arginine reacts with an equimolar amount of an alcohol. However, at least 5 moles of alcohol per mole of $N^2$-dansyl-L-arginine are preferably employed to enhance the reaction rate.

The esterification reaction can be carried out in an inert reaction solvent, such as an aromatic hydrocarbon, e.g., benzene, toluene, xylene, or the like; a chlorinated hydrocarbon, e.g., carbon tetrachloride, chloroform, dichloromethane, or the like; a hydrocarbon solvent, e.g., hexane, cyclohexane, or the like; an ether, e.g., dioxane, tetrahydrofuran, or the like; or a mixture of these compounds. Especially preferred solvents include benzene, toluene, xylene, cyclohexane, carbon tetrachloride, dichloromethane, which form azeotropic mixtures with water, and are therefore advantageous for the esterification reaction, since water formed during the reaction can be easily removed, and the reaction can be carried out advantageously at equilibrium.

The reaction temperature is dependent upon the alcohol to be employed and the activity of the catalyst. Generally, the temperature ranges from 0° C. to the boiling point of the alcohol or solvent. The reaction time varies widely with the species of alcohol employed and the activity of the catalyst and ranges from 10 minutes to 15 hours.

After the reaction is completed, the alcohol and/or solvent is distilled off, and an $N^2$-dansyl-L-arginine ester or an acid addition salt thereof is obtained. Normally, 2 equivalents of acid esterification catalyst addes to the $N^2$-dansyl-L-arginine ester. The acid addition salt can be converted to the corresponding $N^2$-dansyl-L-arginine ester by adjusting the pH of the medium.

$N^2$-dansyl-L-arginine esters and acid addition salts thereof can be purified by recrystallization from a combination of solvents, such as ethyl ether, alcohols, acetone or the like, or reprecipitating by addition of ether to an alcohol solution of the compounds.

(iii) Esterification of $N^2$-dansyl-L-arginine by the reaction of $N^2$-dansyl-L-arginine with an alcohol and a thionyl halide Suitable thionyl halides include thionyl chloride and thionyl bromide. $N^2$-dansyl-L-arginine reacts with an equimolar amount of thionyl halide. However, at least 2 moles of thionyl halide per one mole of $N^2$-dansyl-L-arginine are desirable in order to drive the reaction to completion. During the reaction, the thionyl halide decomposes to a hydrogen halide and $SO_2$, and the formed hydrogen halide adds to the $N^2$-dansyl-L-arginine ester to form a dihalogeno acid salt of the $N^2$-dansyl-L-arginine ester.

The other reaction conditions and the procedures for separation and purification of the product are the same as in process (ii) (esterification with an esterification catalyst).

(iv) Preparation of $N^2$-dansyl-L-arginine methyl ester $N^2$-dansyl-L-arginine methyl ester can be prepared by the reaction of $N^2$-dansyl-L-arginine with diazomethane; reaction of $N^2$-dansyl-L-arginine with dimethyl sulfite and tosylsulfonic acid; and reaction of $N^2$-dansyl-L-arginine with dimethyl sulfate.

(v) Reaction of an alkali metal salt of $N^2$-dansyl-L-arginine with an alkyl halide Alkyl esters of $N^2$-dansyl-L-arginine can be prepared by reacting an alkali metal salt of $N^2$-dansyl-L-arginine and an alkyl halide in a polar solvent.

In addition, $N^2$-dansyl-L-arginine may be esterified by other processes, but processes (ii) and (iii) are generally used.

(vi) Reaction of an L-arginine ester with a dansyl halide

L-arginine esters or acid addition salts thereof, which are used as the starting materials of $N^2$-dansyl-L-arginine esters or acid addition salts thereof, are most generally obtained by reacting L-arginine with an alcohol in the presence of an acid catalyst. When the esterification is carried out in the presence of an acid catalyst, an acid addition salt of an L-arginine ester is usually obtained.

Suitable dansyl halides includes dansyl chloride, dansyl bromide or the like. Dansyl chloride is preferred.

The reaction between an L-arginine ester or an acid addition salt thereof and a dansyl halide is normally carried out in the presence of a base. The base captures the hydrogen halide formed during the reaction and enhances the reaction rate.

Suitable bases include organic bases, such as triethylamine, pyridine, or the like; and common inorganic bases such as sodium hydroxide, potassium hydroxide, potassium carbonate, or the like. The inorganic bases are usually used in aqueous solution.

The base is normally used in an amount at least equivalent to the L-arginine ester. When an acid addition salt of an L-arginine ester is used as the starting material, an excess of base sufficient to convert the L-arginine ester acid addition salt to the L-arginine ester is desirably used in addition to the amount to be used as the catalyst.

The dansyl halide reacts with an equimolar amount of an L-arginine ester or an acid addition salt thereof. The reaction between an L-arginine ester or an acid addition salt thereof and a dansyl halide is usually carried out in a solvent. Suitable solvents include water, chlorinated solvents, such as dichloromethane, chloroform, carbon tetrachloride, and the like; aromatic hydrocarbons, such as benzene, toluene, xylene and the like; esters such as ethyl ether, tetrahydrofuran, tetrahydropyran and the like; ketones such as acetone, methyl ethyl ketone, cyclohexanone and the like; basic solvents, such as dimethylacetamide, dimethylformamide, tetramethylurea, N-methylpyrrolidone, pyridine, quinoline, and the like; or a mixture of two or more of these solvents. A basic solvent acts as an acid acceptor, and therefore addition of base is unnecessary when such solvent is used.

The reaction temperature is dependent on the species of arginine esters and bases, but is generally between 0° C. and the boiling temperature of the solvent employed.

The reaction time varies with the species of the arginine ester and is usually between 10 minutes and 15 hours.

After the reaction is completed, the produced salt is washed away with water, the solvent is removed by distillation, and the obtained product is washed with water and/or the solvent. To the thus obtained $N^2$-dansyl-L-arginine ester, ether and an acid (e.g., hydrochloric acid, p-toluene-sulfonic acid, or the like) are added, and the formed acid addition of salt of $N^2$-dansyl-L-arginine ester is isolated.

(2) Preparation of $N^2$-dansyl-L-argininamides (a) Reaction of an $N^2$-dansyl-L-arginine ester with a primary amine Suitable $N^2$-dansyl-L-arginine esters or the acid addition salts thereof, include the methyl ester, ethyl ester, isopropyl ester and the like or the hydrochlorides thereof. Suitable amines include primary amines, such as an alkylamine containing not more than 10 carbon atoms, e.g., methylamine, ethylamine, n-propylamine, isopropylamine, n-butylamine, n-hexylamine, n-heptylamine and the like; an aralkylamine containing not more than 10 carbon atoms, e.g., $\beta$-phenylethylamine and the like; a cycloalkylamine containing not more than 10 carbon atoms, e.g., cyclopropylamine, cyclobutylamine, cyclopentylamine, cyclohexylamine, cyclooctylamine, 4-methylcyclohexylamine, and the like; an alkylamine containing not more than 10 carbon atoms substituted by an alkoxy group containing not more than 10 carbon atoms, e.g., 2-methoxyethylamine, 2-ethoxyethylamine, 3-methoxypropylamine, 3-methoxybutylamine, 3-methoxypentylamine and the like; a cycloalkylalkylamine containing not more than 10 carbon atoms, e.g., cyclohexylmethylamine, 2-cyclohexylethylamine, cyclobutylmethylamine, 3-cyclopentylbutylamine and the like, and an alkenylamine containing not more than 10 carbon atoms, e.g., allylamine, crotylamine, 3-butenylamine and the like.

The amine is preferably used in an amount equivalent to or greater than the $N^2$-dansyl-L-arginine ester. The amine is preferably used in excess in order to enhance the reaction rate and to carry out the reaction advantageously at eqyilibrium. The amine is usually used in an amount 2 to 10 times the molar quantity of the $N^2$-dansyl-L-arginine ester. When an acid addition salt of an $N^2$-dansyl-L-arginine ester is used, the amine is usually converted to an acid addition salt. Therefore, it is necessary to use an amine corresponding to the acid addition salt of the amine to be formed in excess.

A basic compound may be used as a catalyst. Specifically, an alkali metal alkoxide, such as sodium methoxide or a tertiary amine, such as pyridine or the like are preferable. When these catalysts are used, the reaction rate is enhanced and therefore the amine can be used in a lesser amount and milder reaction conditions are thus possible.

If the amine is used in large excess, $N^2$-dansyl-L-arginine esters or acid addition salts thereof will dissolve in the amine, and therefore the reaction will proceed without a solvent. However, solvents, such as alcohols, e.g., methanol, ethanol, butanol and the like, ethers, e.g., ethyl ether, tetrahydrofuran, tetrahydropyran, dioxane and the like; hydrocarbons, e.g., benzene, toluene, cyclohexane and the like; halogenated hydrocarbons, e.g., carbon tetrachloride, chloroform, dichloromethane and the like; and water can be used.

The reaction is usually carried out by mixing an $N^2$-dansyl-L-arginine ester or an acid addition salt thereof with an excess amount of an amine, the resulting homogeneous solution is allowed to stand at room temperature. However, the reaction mixture can be heated to a temperature up to the boiling temperature of the amine or solvent to enhance the reaction rate.

The reaction time is dependent on the basicity and amount of amine employed, among other factors, but usually ranges from several hours to several days.

After the reaction is completed, the product is collected by filtration, washed with water, and purified by recrystallization from a suitable solvent, e.g., aqueous methanol, or the like. If solid product does not form, the excess amine and/or the solvent is removed by distillation, and the residue is washed and purified by recrystallization from a suitable solvent.

(b) Reaction of an L argininamide with a dansyl halide

An L-argininamide or an acid addition salt thereof can be obtained by protecting the guanidino and $\alpha$-amino group of the arginine via nitration, acetylation, formylation, phthaloylation, trifluoroacetylation, p-methoxybenzyloxycarbonylation, benzoylation, benzyoxycarbonylation, t-butyloxycarbonylation or tritylation and then condensing the obtained arginine derivative with an amine by a conventional process such as the acid chloride process, acid azide process, mixed acid anhydride process, activated esterification process, carbodiimide process, or the like, and thereafter removing the protective group.

Suitable dansyl halides include dansyl chloride, dansyl bromide or the like, but dansyl chloride is preferred.

The reaction between an L-argininamide or an acid addition salt thereof and a dansyl halide is usually carried out in the presence of a base. The basic compound captures the hydrogen chloride, which is formed during the reaction, and thus promotes the reaction.

Suitable bases include organic bases such as triethylamine, pyridine and the like; or inorganic bases, such as sodium hydroxide, potassium hydroxide, potassium carbonate and the like. Inorganic bases are usually used in aqueous solution.

The base is used in excess of the amount equivalent to the L-argininamide. When an acid addition salt of an L-argininamide is used, a base is preferably used in an amount sufficient to convert the acid addition salt of the L-argininamide to the free L-argininamide in addition to the amount of base to be used as the catalyst.

A dansyl halide is usually reacted with an equimolar amount of an L-argininamide or an acid addition salt thereof in a solvent. Suitable solvents include chlorinated hydrocarbons such as dichloromethane, chloroform, carbon tetrachloride and the like; aromatic hydrocarbons, such as benzene, toluene, xylene and the like; ethers, such as ethyl ether, tetrahydrofuran, dioxane, tetrahydropyran and the like; ketones, such as acetone, methyl ethyl ketone, cyclohexanone and the like; basic solvents, such as dimethyl acetamide, dimethylformamide, tetramethylurea, N-methylpyrrolidone, pyridine, quinoline and the like; or a mixture of two or more of these solvents. A basic solvent acts as an acid acceptor, and therefore addition of further base is not required in these instances.

The reaction temperature is dependent on the species of the L-argininamide and base, but usually ranges between 0° C. and the boiling temperature of the solvent. The reaction time varies with the species of the L-argininamide and is usually between 10 minutes and 15 hours.

After the reaction is completed, the formed salt is removed by washing with water, the solvent is removed by distillation, and the obtained product is washed with water and/or the solvent, and the $N^2$-dansyl-L-argininamide is obtained. The thus obtained $N^2$-dansyl- L-argininamide can be isolated in the form of an acid addition salt thereof by addition of ethyl ether and an acid (e.g., hydrochloric acid, p-toluenesulfonic acid, and the like).

(c) Elimination of the $N^G$-substituent from an $N^G$-substituted-$N^2$-dansyl-L-argininamide having the formula (II)

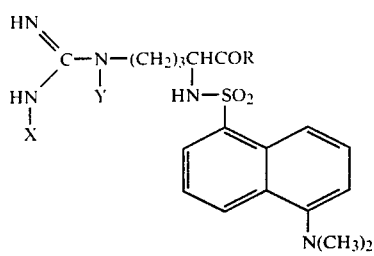

An $N^2$-dansyl-L-argininamide is prepared by eliminating the $N^G$-substituent from an $N^G$-substituted-$N^2$-dansyl-L-argininamide having the above formula (II) by decomposition with an acid or by means of hydrogenation. In the formula (II), R is the same as in the formula (I), X and Y are hydrogen and protective groups for the guanidino group. At least one of X and Y is nitro, tosyl, trityl and oxycarbonyl. Specific examples of R in the formula (II) are as follows:

(1) In the case where R =

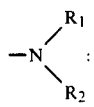

$R_1$ and $R_2$ are respectively an alkyl group containing not more than 10 carbon atoms, e.g., methyl, ethyl, n-propyl, isopropyl, n-butyl, isobutyl, n-pentyl, n-hexyl, n-heptyl and the like; an aryl group containing not more than 10 carbon atoms, e.g., phenyl, tolyl and the like; an aralkyl group containing not more than 10 carbon atoms, e.g., benzyl, phenethyl, 3-phenylpropyl and the like; a cycloalkyl group containing not more than 10 carbon atoms, e.g., cyclopropyl, cyclohexyl and the like; a cycloalkylalkyl group containing not more than 10 carbon atoms, e.g., cyclohexylmethyl, 3-cyclohexylpropyl and the like; an alkenyl group containing not more than 10 carbon atoms, e.g., allyl, crotyl, 2-hexenyl and the like; an alkyl group containing not more than 10 carbon atoms substituted by an alkoxy group, an alkoxycarbonyl group, an acyl group, an acyloxy group, an arylcarbamoyl group or an N,N-polymethylenecarbamoyl group, respectively containing not more than 10 carbon atoms or a carboxyl group, e.g., methoxyethyl, methoxypropyl, ethoxyethyl, ethoxycarbonylmethyl, 2-ethoxycarbonylethyl, 2-methoxycarbonylethyl, 3-ethoxycarbonylpropyl, 2-acetylethyl, 2-acetoxyethyl, 2-phenylcarbamoylethyl, or N,N-tetramethylenecarbamoylmethyl.

(2) In the case where R =

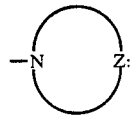

R may be a 1-polymethyleneiminyl group or an oxo-substituted group thereof containing not more than 10 carbon atoms, a 1-polymethyleneiminyl group containing not more than 10 carbon atoms substituted with an alkyl, acyl, alkoxy, or alkoxycarbonyl group containing not more than 10 carbon atoms, e.g., azetidinyl, 3-methoxy-1azetidinyl, 3-ethoxy-1-azetidinyl, 1-pyrrolidinyl, 2-ethoxycarbonyl-1-pyrrolidinyl, 1-(2-pyrrolidonyl), 1-piperidino, 1-(4-piperidonyl), 4-methyl-1-piperidino, 4-ethyl-1-piperidino, 4-n-propyl-1-piperidino, 4-isopropyl-1-piperidino, 2-methyl-1-piperidino, 3-methyl-1-piperidino, 2-ethoxycarbonyl-1-pyrrolidinyl, 4-methoxy-1-piperidino, 4-oxo-1-piperidino, 4-acetyl-1-piperidino, 4-methoxycarbonyl-1-piperidino, 4-carbamoyl-1-piperidino, 1-hexamethyleneiminyl, 1-octamethyleneiminyl and the like; an oxazole or thiazole, such as 3-oxazolidinyl, 3-thiazolidinyl, and the like; an isoxazole or isothiazole, such as 2-isoxazolidinyl, 2-isothiazolidinyl, and the like; an oxazine, such as 4-morpholino, 2,6-dimethyl-4-morpholino, and an oxazine group represented by n-(tetrahydro-1,n-oxazinyl), such as 3-(tetrahydro-1,3-oxazinyl and the like; a thiazine, such as 4-(tetrahydro-1,4-thiazinyl) and the like; 4-methyl-1-piperazinyl, 4-acetyl-1-piperazinyl, 1-piperazinyl, 2-isoindolinyl, 1-indolinyl, 1,2,3,4-tetrahydro-2-isoquinolyl, 4(4-azabicyclo-[3,2,2]-nonyl), 1,2,3,4-tetrahydro-1-quinolyl and the like.

In formula (II), X and Y respectively represent a hydrogen atom or a protective group for the guanidino group, and at least one of X and Y is a protective group for the guanidino group. Suitable protective groups include nitro, tosyl, trityl, or an oxycarbonyl, such as benzyloxycarbonyl, p-nitrobenzyloxycarbonyl, p-methoxybenzyloxycarbonyl, tert-butyloxycarbonyl and the like.

The $N^G$-substituted-$N^2$-dansyl-L-argininamides as represented by general formula (II) or acid addition salts thereof can be obtained by condensing an $N^G$-substituted-$N^2$-substituted-arginine (usually the $N^2$-substituent is a protective group for the amino group, such as benzyloxycarbonyl, t-butyloxycarbonyl, or the like) and an amine via the acid azide process, mixed acid anhydride process, activated esterification process, carbodiimido process or the like, selectively removing only the $N^2$-substituent by means of catalytic hydrogenation or acid decomposition, and reacting the thus obtained $N^G$-substituted-L-argininamide or an acid addition salt thereof with a dansyl halide, such as dansyl chloride in the presence of a base in a solvent. Suitable bases include organic bases, such as triethylamine, pyridine and the like; or inorganic bases, such as sodium hydroxide, potassium hydroxide, potassium carbonate, sodium hydrogen carbonate and the like. Inorganic bases are normally used in aqueous solution.

The base is preferably used in an amount not less than the amount equivalent to the $N^G$-substituted-L-argininamide. When an acid addition salt of an $N^G$-substituted-L-argininamide is used, the base is preferably used in an amount sufficient to neutralize the acid addition salt in addition to the amount to be used as the catalyst. The dansyl halide is normally used in an equimolar amount.

Suitable solvents include water; chlorinated solvents, such as dichloromethane, chloroform, carbon tetrachloride and the like; aromatic hydrocarbons, such as benzene, toluene, xylene and the like; ethers, such as ethyl ether, tetrahydrofuran, dioxane and the like; ketones, such as acetone, methyl ethyl ketone, cyclohexanone, and the like; basic solvents, such as dimethylacetamide, dimethylformamide, tetramethylurea, N-methylpyrrolidone, pyridine, quinoline, and the like; or a mixture of two or more of the above-mentioned solvents. A basic solvent acts as an acid acceptor, and therefore further addition of base is not required in these instances.

The reaction temperature is dependent on the species of $N^G$-substituted-L-argininamide and base, but usually ranges from $-10°$ C. to the boiling temperature of the solvent.

The reaction time varies with the species of $N^G$-substituted-L-argininamide and base, and the reaction temperature, and is usually from 5 minutes to 24 hours.

After the reaction is completed, the solvent and base are distilled off, the formed salt is removed by washing with water, and the $N^G$-substituted-$N^2$-dansyl-L-argininamide is purified by recrystallizing or reprecipitating from a suitable solvent. The reaction product may also be separated and purified by means of chromatography. Suitable elutants include chlorinated solvents, such as chloroform, dichloromethane and the like; a chlorinated solvent containing alcohol and the like.

As explained above, $N^2$-dansyl-L-argininamide represented by general formula (II) or an acid addition salt thereof is obtained from $N^G$-substituted-$N$-$^2$-dansyl-L-argininamide by removing the $N^G$-substituent, which is a protective group for the guanidino group of the amide, via hydrogenation or acid decomposition.

Suitable acids for the acid decomposition include hydrogen halides, such as hydrogen chloride, hydrogen bromide, hydrogen fluoride; and organic acids, such as trifluoroacetic acid, trifluoromethanesulfonic acid, formic acid, acetic acid, and the like.

The acid decomposition is preferably carried out by treating an $N^G$-substituted-$N^2$-dansyl-L-argininamide or an acid addition salt thereof with any of the above-mentioned acids without a solvent or in a solvent, such as an alcohol, e.g., methanol, ethanol and the like; an ether, e.g., tetrahydrofuran, dioxane, and the like; an organic acid, e.g., acetic acid and the like; or an ester, e.g., ethyl acetate and the like, at a temperature between $31\ 10°$ C. and $100°$ C., preferably at room temperature. The time required for the acid decomposition varies with the species of the acid and solvent, the protective $N^G$-substituent, and the temperature of treatment, and is from 30 minutes to 24 hours.

After the decomposition is completed, the $N^2$-dansyl-L-argininamide or an acid addition salt thereof is obtained by removing the solvent and the excess acid or adding to the reaction mixture an inert solvent, such as ethyl ether, petroleum ether, a hydrocarbon solvent, or the like so as to form a precipitate and collecting the precipitate. An excess of acid is usually used, and therefore the $N^2$-dansyl-L-argininamide which is obtained by removing the protective group is in the form of an acid addition salt. This salt can be easily converted to a free amide by neutralization.

Hydrogenation can be carried out according to the general procedures of reductive hydrogenation, although catalytic hydrogenation is most advantageous. Catalytic hydrogenation is carried out in the presence of a hydrogen-activating catalyst in a hydrogen atmosphere. Suitable hydrogen-activating catalysts include Raney nickel, palladium, platinum and the like. Suitable solvents include alcohols, such as methanol, ethanol and the like; ethers, such as dioxane, tetrahydrofuran and the like; organic acids, such as acetic acid, propionic acid and the like; or a mixture of two or more of the above-mentioned solvents.

The reaction temperature is dependent on the protective group for the guanidino group and the activity of the employed catalyst, and is usually between $0°$ C. and the boiling temperature of the solvent. The hydrogen pressure is dependent on the reaction temperature and activity of the employed catalyst. Atmospheric pressure is sufficient for the reaction. The reaction time is dependent on the activity of the catalyst, the reaction temperature, hydrogen pressure and the like and is usually from 2 hours to 120 hours.

After the hydrogenation is finished, the catalyst is removed by filtration, the solvent is removed by distillation, and the $N^2$-dansyl-L-argininamide or an acid addition salt thereof is obtained. The acid addition salt is easily converted to the free $N^2$-dansyl-L-argininamide by neutralization.

The thus obtained $N^2$-dansyl-L-argininamide or acid addition salt thereof is purified by recrystallizing from a solvent which is a mixture of two or more of the following: water, ethyl ether, alcohols, acetone, or the like, or by reprecipitating by addition of ethyl ether to an alcohol solution of the compound.

$N^2$-dansyl-L-arginine esters and amides of this invention having the formula (I) form acid addition salts with any of a variety of inorganic and organic acids. The product of the reactions described above can be isolated as the free base or as the acid addition salt. In addition, the product can be obtained as pharmaceutically acceptable acid addition salts by reacting one of the free bases with an acid, such as hydrochloric, hydrobromic, hydroiodic, nitric, sulfuric, phosphoric, acetic, citric, maleic, succinic, lactic, tartaric, gluconic, benzoic, methanesulfonic, ethanesulfonic, benzensulfonic, p-toluenesulfonic acid or the like.

As stated above, $N^2$-dansyl-L-arginine esters and amides, and acid addition salts thereof of this invention are characterized by highly specific inhibitory activity against thrombin, and therefore these compounds are useful in the determination of thrombin in blood as diagnostic reagents, and/or for the medical control or prevention of thrombosis.

The antithrombotic activities of the $N^2$-dansyl-L-arginine derivatives of this invention were compared with those of a known antithrombotic agent, ($N^2$-(p-tolylsulfonyl)-L-arginine methyl ester), by determining the fibrinogen coagulation time. The measurement of the fibrinogen coagulation time was conducted as follows:

An 0.8 ml aliquot of a fibrinogen solution, which had been prepared by dissolving 150 mg of bovine fibrinogen (Cohn fraction I) supplied by Armour Inc. in 40 ml of a borate saline buffer (pH 7.4), was mixed with 0.1 ml of a borate saline buffer, pH 7.4, (control) or a sample solution in the same buffer, and 0.1 ml of a thrombin solution (5 units/ml) supplied by Mochida Pharmaceutical Ltd. was added to the solutions in an ice bath. Immediately after mixing, the reaction mixture was transferred from the ice bath to a bath thermostated at $25°$ C. Coagulation times were taken as the period between the time of transference to the $25°$ C. bath and the time of the first appearance of fibrin threads. In the cases where no drug samples were added, the coagulation time was 50–55 seconds.

The experimental results are summarized in Table 1. The term "concentration required to prolong the coagulation time by a factor of two" is the concentration of an active ingredient require to prolong the normal coagulation time 50–55 seconds to 100–110 seconds.

The inhibitors are shown in Table 1 by indicating R in the general formula (II) and the added acid and/or water of crystallization.

When a solution containing an $N^2$-dansyl-L-arginine derivative of this invention was administered intravenously into animal bodies, the high antithrombotic activity in the circulating blood was maintained for from one to three hours. The halflife for decay of the antithrombotic compounds of this invention in circulating blood was shown to be approximately 30 minutes; the physiological conditions of the host animals were well maintained. The experimental decrease of fibrinogen in animals caused by infusion of thrombin was satisfactorily controlled by simultaneous infusion of the compounds of this invention.

The acute toxicity values ($LD_{50}$) determined by oral administration of substances of formula (I) in mice range from about 1,000 to 10,000 milligrams per kilogram of body weight. Representative $LD_{50}$ values, for example, for $N^2$-dansyl-L-arginine n-butyl ester, 4-methyl-1-($N^2$-dansyl-L-arginyl)piperidine, 4-ethyl-1-($N^2$-dansyl-L-arginyl)piperidine, 2-($N^2$-dansyl-L-arginyl)-isoindoline are >6000, 1310, 1375, 1360 milligrams per kilogram, respectively.

The therapeutic agents of this invention may be administered alone or in combination with pharmaceutically acceptable carriers, the proportion of which is determined by the solubility and chemical nature of the compound, chosen route of administration and standard pharmaceutical practice. For example, the compounds may be injected parenterally, that is, intramuscularly, intravenously or subcutaneously. For parenteral administration, the compounds may be used in the form of sterile solutions containing other solutes, for example, sufficient saline or glucose to make the solution isotonic. The compounds may be administered orally in the form of tablets, capsules, or granules containing suitable excipients such as starch, lactose, white sugar and the like. The compounds may be administered sublingually in the form of troches or lozenges in which each active ingredient is mixed with sugar or corn syrups, flavoring agents and dyes, and then dehydrated sufficiently to make the mixture suitable for pressing into solid form. The compounds may be administered orally in the form of solutions which may contain coloring and flavoring agents.

Physicians will determine the dosage of the present therapeutic agents which will be most suitable, and dosages vary with the mode of administration and the particular compound chose. In addition, the dosage will vary with the particular patient under treatment.

When the composition is administered orally, a larger quantity of the active agent will be required to produce the same effect as caused with a smaller quantity given parenterally. The therapeutic dosage is generally 10–50 mg/kg of active ingredient parenterally, 10–500 mg/kg orally per day.

Having generally described the invention, a more complete understanding can be obtained by reference to certain specific examples, which are included for purposes of illustration only and are not intended to be limiting unless otherwise specified.

EXAMPLE 1

To an ice-cooled suspension of 1.0 gram of $N^2$-dansyl-L-arginine in 15 ml of methanol was added dropwise 0.5 ml of thionyl chloride with vigorous stirring. After being allowed to stand for 2 hours at room temperature, the reaction mixture was refluxed for 2 hours, and was evaporated to dryness (syrup). Treatment of the residual syrup with cold ethyl ether and a small amount of water gave crude crystals. After recrystallization from methanol-ethyl ether, colorless $N^2$-dansyl-L-arginine methyl ester dihydrochloride monohydrate was obtained in 92% yield: mp. 147°–150° C.

| Elemental analysis (as $C_{19}H_{29}O_4N_5S \cdot HCl \cdot H_2O$) | | | |
|---|---|---|---|
| | C | H | N |
| Calculated: | 44.62 | 6.11 | 13.69 |
| Found: | 44.42 | 6.17 | 13.64 |

EXAMPLE 2

A suspension of 1.0 gram of $N^2$-dansyl-L-arginine in 15 ml of anhydrous ethanol was saturated with dry hydrogen chloride for 1 hour. The reaction mixture was refluxed for an additional one hour. After cooling, the reaction mixture was concentrated in vacuo. The residue was triturated with cold ethyl ether to give a crystalline product. After crystallization from ethanol-ethyl ether, $N^2$-dansyl-L-arginine ethyl ester dihydrochloride was obtained in 95% yield; mp. 140°–144° C.

| Elemental analysis (as $C_{20}H_{29}O_4N_5S \cdot 2HCl$) | | | |
|---|---|---|---|
| | C | H | N |
| Calculated: | 47.24 | 6.15 | 13.77 |
| Found: | 46.95 | 6.21 | 14.00 |

EXAMPLE 3

A mixture of 1.0 grams of $N^2$-dansyl-L-arginine and 1.4 gram of p-toluenesulfonic acid monohydrate in 10 ml of benzyl alcohol was heated for 30 minutes at 100° C. To the thus obtained clear solution, 100 ml of benzene was added, and the mixture was refluxed for 5 hours, removing water by azeotropic distillation. After the solvent was removed by distillation, 100 ml of ethyl ether was added to the residue, giving a crystalline mass. Crystallization from acetone gave $N^2$-dansyl-L-arginine benzyl ester di(p-toluenesulfonate) in 87% yield; mp. 150°–153° C.

| Elemental analysis (as $C_{25}H_{31}O_4N_5S \cdot C_{14}H_{16}O_6S_2$) | | | |
|---|---|---|---|
| | C | H | N |
| Calculated: | 55.63 | 5.63 | 8.32 |
| Found: | 55.33 | 5.61 | 8.19 |

EXAMPLE 4

A mixture of 1.0 gram of $N^2$-dansyl-L-arginine and 1.4 gram of p-toluenesulfonic acid monohydrate in 10 ml of 2-ethylhexanol was heated for 30 minutes at 100° C. To the thus obtained clear solution, 100 ml of benzene was added, and the mixture was refluxed for 10 hours, removing water by azeotropic distillation. After the solvent was removed by distillation, 100 ml of ethyl ester was added to the residue to give a crystalline mass. Crystallization from acetone gave $N^2$-dansyl-L-arginine 2-ethylhexyl ester di(p-toluenesulfonate) in 91% yield; mp. 170°–174° C.

| Elemental analysis (as $C_{26}H_{41}O_4N_5S.C_{14}H_{16}O_6S_2$) | | | |
|---|---|---|---|
| | C | H | N |
| Calculated: | 55.60 | 6.65 | 8.11 |
| Found: | 55.37 | 6.59 | 8.18 |

EXAMPLE 5

To an ice-cooled suspension of 1.0 gram of $N^2$-dansyl-L-arginine in 15 ml of isopropanol was added dropwise 0.5 ml of thionyl chloride with vigorous stirring. After being allowed to stand for 2 hours at room temperature, the reaction mixture was refluxed for 4 hours, and was evaporated to dryness (syrup). Treatment of the residual syrup with cold ethyl ether gave crude crystals. After recrystallization from isopropanol-ethyl ether, colorless $N^2$-dansyl-L-arginine isopropyl ester dihydrochloride was obtained in 90% yield; mp. 110°–120° C.

| Elemental analysis (as $C_{21}H_{31}O_4N_5S.2HCl$) | | | |
|---|---|---|---|
| | C | H | N |
| Calculated: | 48.27 | 6.37 | 13.40 |
| Found: | 47.90 | 6.08 | 13.21 |

EXAMPLE 6

A mixture of 1.0 gram of $N^2$-dansyl-L-arginine and 1.4 gram of p-toluenesulfonic acid monohydrate in 10 ml of n-hexyl alcohol was heated for 30 minutes at 100° C. To the thus obtained clear solution, 100 ml of benzene was added, and the mixture was refluxed for 3 hours, removing water by azeotropic distillation. After the solvent was removed by distillation, 50 ml of ethyl ether and 50 ml of petroleum ether were added to the residue to give a crystalline mass. Crystallization from acetone gave $N^2$-dansyl-L-arginine-n-hexyl ester di(p-toluenesulfonate) in 95% yield; mp. 190°–193° C.

| Elemental analysis (as $C_{24}H_{30}O_4N_5S.C_{14}H_{16}O_6S_2$) | | | |
|---|---|---|---|
| | C | H | N |
| Calculated: | 54.59 | 6.39 | 8.38 |
| Found: | 54.33 | 6.48 | 8.11 |

EXAMPLE 7

A mixture of 1.0 gram of $N^2$-dansyl-L-arginine and 1.0 gram of p-toluenesulfonic acid monohydrate in 10 ml of n-butyl alcohol was heated for 30 minutes at 100° C. To the thus obtained clear solution, 100 ml of benzene was added, and the mixture was refluxed for 3 hours, removing water by azeotropic distillation. After the solvent was removed by distillation, 50 ml of ethyl ether and 50 ml of petroleum ether were added to the residue to give a crystalline mass. Crystallization from acetone gave $N^2$-dansyl-L-arginine-n-butyl ester di(p-toluenesulfonate) in 95% yield; mp. 160°–164° C.

| Elemental analysis (as $C_{22}H_{33}O_4N_5S.C_{14}H_{16}O_6S_2$) | | | |
|---|---|---|---|
| | C | H | N |
| Calculated: | 53.51 | 6.11 | 8.67 |
| Found: | 53.32 | 6.14 | 8.93 |

EXAMPLE 8

A mixture of 1.0 gram of $N^2$-dansyl-L-arginine and 1.0 gram of p-toluenesulfonic acid monohydrate in 10 ml of n-amyl alcohol was heated for 30 minutes at 100° C. To the thus obtained clear solution, 100 ml of benzene was added, and the mixture was refluxed for 4 hours, removing water by azeotropic distillation. After the solvent was removed by distillation, 100 ml of petroleum ether was added to the residue to give a crystalline mass. Crystallization from acetone gave $N^2$-dansyl-L-arginine n-amyl ester di(p-toluenesulfonate) in 96% yield; mp. 164°–169° C.

| Elemental analysis (as $C_{23}H_{35}O_4N_5S.C_{14}H_{16}O_6S_2$) | | | |
|---|---|---|---|
| | C | H | N |
| Calculated: | 54.06 | 6.25 | 8.52 |
| Found: | 53.86 | 6.10 | 8.53 |

EXAMPLE 9

By the same procedures as described in Example 3, $N^2$-dansyl-L-arginine isobutyl ester di(p-toluenesulfonate) was obtained from $N^2$-dansyl-L-arginine and isobutyl alcohol in 92% yield; mp 146°–151° C.

| Elemental analysis (as $C_{22}H_{33}O_4N_5S.C_{14}H_{16}O_6S_2$) | | | |
|---|---|---|---|
| | C | H | N |
| Calculated: | 53.51 | 6.11 | 8.67 |
| Found: | 53.54 | 6.11 | 8.65 |

EXAMPLE 10

By the same procedures as described in Example 3, $N^2$-dansyl-L-arginine isopentyl ester di(p-toluenesulfonate) was obtained from $N^2$-dansyl-L-arginine and isopentyl alcohol in 94% yield; mp. 163°–168° C.

| Elemental analysis (as $C_{23}H_{35}O_4N_5S.C_{14}H_{16}O_6S_2$) | | | |
|---|---|---|---|
| | C | H | N |
| Calculated: | 54.06 | 6.25 | 8.52 |
| Found: | 53.74 | 6.09 | 8.57 |

EXAMPLE 11

A mixture of 1.0 gram of $N^2$-dansyl-L-arginine and 1.4 gram of p-toluenesulfonic acid monohydrate in 10 ml of 3-chloro-1-propanol was heated for 30 minutes at 100° C. To the thus obtained clear solution, 100 ml of benzene was added, and the mixture was refluxed for 5 hours, removing water by azeotropic distillation. After the solvent was removed by distillation, 100 ml of ethyl ether was added to the residue to give a crystalline mass. Crystallization from acetone gave $N^2$-dansyl-L-arginine 3-chloropropyl ester di(p-toluenesulfonate) in 88% yield; mp. 140°–145° C.

| Elemental analysis (as $C_{21}H_{30}O_4N_5ClS.C_{14}H_{16}O_6S_2$) | | | |
|---|---|---|---|
| | C | H | N |
| Calculated: | 50.74 | 5.60 | 8.45 |
| Found: | 50.30 | 5.50 | 8.01 |

EXAMPLE 12

To a solution of 1.0 gram of L-arginine methyl ester dihydrochloride in 50 ml of dichloromethane and 1.15 gram of triethylamine, was added 1.03 gram of dansyl chloride with stirring at room temperature. After being stirred for 5 hours at room temperature, the reaction mixture was poured into 30 ml of water.

After separation of the aqueous layer, the dichloromethane solution was dried over anhydrous $Na_2SO_4$. The $Na_2SO_4$ was filtered off, and the solution was evaporated under reduced pressure to give $N^2$-dansyl-L-arginine methyl ester. To the solid was added ethyl ester saturated with dry hydrogen chloride, and $N^2$-dansyl-L-arginine methyl ester dihydrochloride monohydrate was obtained in 83% yield; mp. 147°–150° C. (decomp).

| Elemental analysis (as $C_{19}H_{29}O_4N_5S.2HCl.H_2O$) | | | |
|---|---|---|---|
| | C | H | N |
| Calculated: | 44.62 | 6.11 | 13.69 |
| Found: | 44.32 | 6.00 | 13.39 |

EXAMPLE 13

To a mixture of 1.5 gram of L-arginine n-butyl ester dihydrochloride and 1.4 gram of $K_2CO_3$ in 10 ml of water was added dropwise a solution of 1.34 gram of dansyl chloride in 20 ml of ethyl ester with vigorous stirring at 0°–5° C. over a period of 30 minutes. After the solution was kept at room temperature for 10 hours with stirring a viscous deposit separated, which was collected and triturated with water and ethyl ether.

To a suspension of the resulting product in 20 ml of ethyl ether was added 2 grams of p-toluenesulfonic acid monohydrate with stirring to yield crystals. Recrystallization from acetone gave 3.60 gram of $N^2$-dansyl-L-arginine n-butyl ester di(p-toluenesulfonate) in 89.1% yield; mp. 160°–163° C.

| Elemental analysis (as $C_{22}H_{33}O_4N_5S.C_{14}H_{16}O_6S_2$) | | | |
|---|---|---|---|
| | C | H | N |
| Calculated: | 53.51 | 6.11 | 8.67 |
| Found: | 53.50 | 6.20 | 8.85 |

EXAMPLE 14

A 1.0 gram amount of $N^2$-dansyl-L-arginine methyl ester dihydrochloride monohydrate was dissolved in 2 ml of n-butylamine with vigorous agitation. After the resulting solution was allowed to stand at room temperature for 2 days, the n-butyl-amine was removed by vacuum distillation and to the residual syrup was added 5 ml of water to obtain a crystalline deposit.

The precipitate was collected and recrystallized from 50% aqueous methanol to give $N^2$-dansyl-N-(n-butyl-(-L-argininamide monohydrate in 90% yield; mp. 150°–152° C.

| Elemental analysis (as $C_{22}H_{34}O_3N_6S.H_2O$) | | | |
|---|---|---|---|
| | C | H | N |
| Calculated: | 54.98 | 7.55 | 17.49 |
| Found: | 54.72 | 7.61 | 17.25 |

EXAMPLE 15

A 1.0 gram amount of $N^2$-dansyl-L-arginine ethyl ester dihydrochloride was dissolved in 2 ml of n-propylamine with vigorous agitation. After the resulting solution was allowed to stand at room temperature for 2 days, the n-propylamine was removed by distillation in vacuo and to the residual syrup was added 5 ml of water to obtain a crystalline deposit.

The precipitate was collected and recrystallized from 50% aqueous methanol to give $N^2$-dansyl-N-(n-propyl)-L-argininamide monohydrate in 85% yield; mp. 150°–153° C.

| Elemental analysis (as $C_{21}H_{32}O_3N_6S.H_2O$) | | | |
|---|---|---|---|
| | C | H | N |
| Calculated: | 54.06 | 7.35 | 18.02 |
| Found: | 53.82 | 7.45 | 18.13 |

EXAMPLE 16

A 1.0 gram amount of $N^2$-dansyl-L-arginine methyl ester dihydrochloride monohydrate was dissolved in 2 ml of isopropylamine with vigorous agitation. After the resulting solution was allowed to stand at room temperature for 2 days, the isopropylamine was removed by vacuum distillation and to the residual syrup was added 5 ml of water to obtain a crystalline deposit.

The precipitate was collected and recrystallized from 50% aqueous methanol to give $N^2$-dansyl-N-isopropyl-L-argininamide in 78% yield; mp. 218°–221° C.

| Elemental analysis (as $C_{21}H_{32}O_3N_6S$) | | | |
|---|---|---|---|
| | C | H | N |
| Calculated: | 56.23 | 7.19 | 18.72 |
| Found: | 56.38 | 7.20 | 18.94 |

EXAMPLE 17

A 1.0 gram amount of $N^2$-dansyl-L-arginine isopropyl ester dihydrochloride was dissolved in 3 ml of β-phenylethylamine with vigorous agitation. After the resulting solution was allowed to stand at room temperature for 4 days, the reaction mixture was poured into a mixture of 30 ml of water and 30 ml of ethyl ether to obtain a crystalline deposit.

The precipitate was collected and recrystallized from 50% aqueous methanol to give $N^2$-dansyl-N-(β-phenylethyl)-L-argininamide.dihydrate in 91% yield; mp. 143°–145° C.

| Elemental analysis (as $C_{26}H_{33}O_3N_6S.2H_2O$) | | | |
|---|---|---|---|
| | C | H | N |
| Calculated: | 57.13 | 7.01 | 15.38 |
| Found: | 57.34 | 6.72 | 15.64 |

EXAMPLE 18

To a suspension of 1.0 gram of $N^2$-dansyl-L-arginine methyl ester dihydrochloride monohydrate in 1 ml of tetrahydrofuran was added 3 ml of ethylamine with cooling. The mixture was allowed to stand in a sealed tube at room temperature for three days. After the excess amine was removed by evaporation, the residue was poured into 50 ml of water to give a precipitate.

Recrystallization from 50% aqueous methanol afforded $N^2$-dansyl-N-ethyl-L-argininamide monohydrate in 93% yield; mp. 220°–222° C.

Elemental analysis: (as $C_{20}H_{30}O_3N_6S.H_2O$)

|  | C | H | N |
|---|---|---|---|
| Calculated: | 53.08 | 7.13 | 18.57 |
| Found: | 53.34 | 7.18 | 18.86 |

EXAMPLE 19

A 1.0 gram amount of $N^2$-dansyl-L-arginine methyl ester dihydrochloride monohydrate was dissolved in 3 ml of n-hexylamine with vigorous agitation. After the resulting solution was allowed to stand at room temperature for 2 days, the n-hexylamine was removed by vacuum distillation and to the residual syrup was added 20 ml of water to obtain a crystalline deposit.

The precipitate was collected and recrystallized from 50% aqueous methanol to give $N^2$-dansyl-N-(n-hexyl)-L-argininamide monohydrate in 93% yield; mp. 133°–135° C.

Elemental analysis (as $C_{24}H_{38}O_3N_6S.H_2O$)

|  | C | H | N |
|---|---|---|---|
| Calculated: | 56.67 | 7.93 | 16.53 |
| Found: | 56.38 | 7.59 | 16.34 |

EXAMPLE 20

A 1.0 gram amount of $N^2$-dansyl-L-arginine methyl ester dihydrochloride monohydrate was dissolved in 3 ml of n-heptylamine with vigorous agitation. After the resulting solution was allowed to stand at 80° C. for 5 hours, the reaction mixture was cooled and poured into 30 ml of cold water to obtain a crystalline deposit.

The precipitate was collected and recrystallized from 50% aqueous methanol to give $N^2$-dansyl-N-(n-heptyl)-L-argininamide in 85% yield; mp. 240°–243° C.

Elemental analysis (as $C_{25}H_{40}O_3N_6S$)

|  | C | H | N |
|---|---|---|---|
| Calculated: | 59.50 | 7.99 | 16.66 |
| Found: | 59.50 | 7.90 | 16.68 |

EXAMPLE 21

A 1.0 gram amount of $N^2$-dansyl-L-arginine methyl ester dihydrochloride monohydrate was dissolved in 3 ml of isobutylamine with vigorous agitation. After the resulting solution was allowed to stand at room temperature for 2 days, the reaction mixture was poured into 20 ml of water and was agitated to obtain a crystalline deposit.

The precipitate was collected and recrystallized from 50% aqueous methanol to give $N^2$-dansyl-N-isobutyl-L-argininamide in 80% yield; mp. 157°–160° C.

Elemental analysis (as $C_{22}H_{34}O_3N_6S$)

|  | C | H | N |
|---|---|---|---|
| Calculated: | 57.12 | 7.41 | 18.17 |
| Found: | 56.82 | 7.41 | 17.90 |

EXAMPLE 22

A 1.0 gram amount of $N^2$-dansyl-L-arginine methyl ester dihydrochloride monohydrate was dissolved in 2 ml of 2-methoxyethylamine with vigorous agitation. After the resulting solution was allowed to stand at room temperature for 2 days, the 2-methoxy-ethylamine was removed by vacuum distillation and to the residual syrup was added 5 ml of water to obtain a crystalline deposit.

The precipitate was collected and recrystallized from 50% aqueous methanol to give $N^2$-dansyl-N-(2-methoxyethyl)-L-argininamide dihydrate in 90% yield; mp. 130°–135° C.

Elemental analysis (as $C_{21}H_{32}O_4N_6S.2H_2O$)

|  | C | H | N |
|---|---|---|---|
| Calculated: | 50.38 | 7.25 | 16.79 |
| Found: | 50.03 | 6.95 | 16.99 |

EXAMPLE 23

A 1.0 gram amount of $N^2$-dansyl-L-arginine ethyl ester dihydrochloride was dissolved in 3 ml of cyclohexylmethylamine with vigorous agitation. After the resulting solution was allowed to stand at 80° C. for 5 hours, the reaction mixture was cooled and poured into 30 ml of water to obtain a crystalline deposit.

The precipitate was collected and recrystallized from 50% aqueous methanol to give $N^2$-dansyl-N-cyclohexylmethyl-L-argininamide in 85% yield; mp. 253°–256° C.

Elemental analysis (as $C_{25}H_{38}O_3N_6S$)

|  | C | H | N |
|---|---|---|---|
| Calculated: | 59.73 | 7.62 | 16.72 |
| Found: | 59.96 | 7.48 | 16.73 |

EXAMPLE 24

To a solution of 1.0 gram of N-(2-methoxyethyl)-L-argininamide in 30 ml of dichloromethane and 0.52 gram of triethylamine was added 1.16 gram of dansyl chloride with stirring at room temperature. After stirring for 2 hours at room temperature, the dichloromethane was removed by distillation and the residual syrup was poured into 50 ml of ice water.

After separation of the aqueous layer, the dichloromethane solution was dried over anhydrous $Na_2SO_4$. The $Na_2SO_4$ was filtered off, the solution was evaporated under reduced pressure, and $N^2$-dansyl-N-(2-methoxyethyl)-L-argininamide dihydrate was obtained in 89% yield; mp. 130°–135° C. (decomp).

Elemental analysis (as $C_{21}H_{32}O_4N_6S.2H_2O$)

|  | C | H | N |
|---|---|---|---|
| Calculated: | 50.38 | 7.25 | 16.79 |
| Found: | 50.68 | 6.95 | 16.99 |

EXAMPLE 25

To a mixture of 1.0 gram of 1-(L-arginyl)-piperidine and 0.57 gram of $K_2CO_3$ in 10 ml of water was added dropwise a solution of 1.12 gram of dansyl chloride in 30 ml of dioxane with vigorous stirring over a period of 30 minutes while maintaining the temperature at 0° C. The reaction mixture was stirred for an additional 3 hours and the formed precipitate was removed by filtration. The solvent was evaporated, and to the residue was added 30 ml of $CHCl_3$. A small amount of the undissolved material was filtered and the solution was dried over anhydrous $Na_2SO_4$. To the stirred solution was added 20 ml of ether containing 0.5 gram of acetic acid to precipitate 1-($N^2$-dansyl-L-arginyl)piperidine diacetate, which was purified by reprecipitation from a methanol-ethyl ether mixture in 72% yield.

| Elemental analysis (as $C_{23}H_{34}O_3N_6S.2CH_3COOH$) | | | |
|---|---|---|---|
| | C | H | N |
| Calculated: | 54.53 | 7.12 | 14.13 |
| Found: | 54.23 | 7.11 | 14.43 |

EXAMPLE 26

A 3.2 gram amount of $N^G$-nitro-$N^2$-(tert-butyloxycarbonyl)-L-arginine was dissolved in a mixture of 40 ml of dry tetrahydrofuran and 1.4 ml of triethylamine. To the solution was added 1.4 ml of isobutyl chloroformate with stirring and cooling in an ice-salt bath. After additional stirring for 15 minutes, 0.87 gram of N-methyl-n-butylamine was added to the mixture. Then the reaction mixture was stirred continuously for 40 minutes at room temperature. The solvent was removed by distillation under reduced pressure, below 40° C. The residue was extracted with 100 ml of ethyl acetate and the extract was washed successively with a 10% aqueous citric acid solution, saturated sodium chloride solution, saturated aqueous sodium bicarbonate solution, and finally with saturated aqueous sodium chloride solution. The organic layer was dried over anhydrous $Na_2SO_4$, filtered and concentrated to give $N^G$-nitro-$N^2$-(tert-butyloxy-carbonyl)-N-(n-butyl)-N-methyl-L-argininamide. This material was added to ethyl acetate containing 10% dry HCl and allowed to stand for 2 hours, and $N^G$-nitro-N-(n-butyl)-N-methyl-L-argininamide hydrochloride was precipitated.

To a mixture of 3.0 gram of $N^G$-nitro-N-(n-butyl)-N-methyl-L-argininamide hydrochloride, 30 ml of dichloromethane and 4.1 gram of triethylamine was added 3.0 gram of dansyl chloride with stirring and cooling in an ice-bath. After stirring at 0° C. for 24 hours, 20 ml of water was added to the reaction mixture. After separation of the aqueous layer, the dichloromethane layer was dried over anhydrous $Na_2SO_4$. The $Na_2SO_4$ was removed by filtration and the solution was evaporated to give a viscous oily product. The product was purified by chromatography using chloroform containing 10% methanol as the elutant and silica gel as the carrier. Powdery $N^G$-nitro-$N^2$-dansyl-N-(n-butyl)-N-methyl-L-argininamide was obtained in 73% yield (based on $N^G$-nitro-N-(n-butyl)-N-methyl-L-argininamide hydrochloride).

| Elemental analysis (as $C_{23}H_{35}O_5N_7S$) | | | |
|---|---|---|---|
| | C | H | N |
| Calculated: | 52.96 | 6.76 | 18.48 |
| Found: | 53.12 | 7.09 | 18.27 |

A 1.0 gram amount of $N^G$-nitro-$N^2$-dansyl-N-(n-butyl)-N-methyl-L-argininamide was dissolved in 20 ml of ethanol and 5 ml of acetic acid. A 50 mg amount of palladium catalyst was added and the mixture was shaken in a stream of hydrogen for 100 hours at room temperature. After filtering off the catalyst, the filtrate was evaporated to give a viscous oily product. Reprecipitation from methanol-ethyl ether gave $N^2$-dansyl-N-(n-butyl)-N-methyl-L-argininamide diacetate in powder form in 83% yield.

| Elemental analysis (as $C_{23}H_{36}O_3N_6S.2CH_3COOH$) | | | |
|---|---|---|---|
| | C | H | N |
| Calculated: | 54.35 | 7.43 | 14.09 |
| Found: | 54.33 | 7.43 | 14.00 |

EXAMPLE 27

A 1.0 gram amount of $N^G$-nitro-$N^2$-dansyl-N,N-diethyl-L-argininamide, which was prepared in the same manner as described in Example 26, was dissolved in a mixture of 25 ml of ethanol and 5 ml of acetic acid. A 50 mg amount of palladium black was added and the mixture was shaken in a stream of hydrogen for 50 hours at 30° C. After removal of the catalyst, the solvent was evaporated to obtain a viscous oily residue. Reprecipitation from methanol-ethyl ether gave $N^2$-dansyl-N,N-diethyl-L-argininamide diacetate in powder form in 71% yield.

| Elemental analysis (as $C_{22}H_{34}O_3N_6S.2CH_3COOH$) | | | |
|---|---|---|---|
| | C | H | N |
| Calculated: | 53.59 | 7.27 | 14.42 |
| Found: | 53.99 | 7.30 | 14.82 |

EXAMPLE 28

A 5.4 gram amount of $N^G,N^G$-dibenzyloxycarbonyl-$N^2$-(tertbutyloxy-carbonyl)-L-arginine was dissolved in a mixture of 50 ml of dry tetrahydrofuran and 1.4 ml of triethylamine. To the solution was added 1.4 ml of isobutyl chloroformate with stirring and cooling in an ice-salt bath. After additional stirring for 15 minutes, 1.17 gram of β-alaine ethyl ester was added to the mixture, and the reaction mixture was stirred further for 40 minutes at room temperature. The solvent was removed by distillation under reduced pressure, below 40° C. The residue was extracted with 100 ml of ethyl acetate and the extract was washed successively with 10% aqueous citric acid solution, saturated sodium chloride solution, saturated aqueous sodium bicarbonate solution, and finally with saturated aqueous sodium chloride solution. The organic layer was dried over anhydrous $Na_2SO_4$, filtered and concentrated to give $N^G$, $N^G$-dibenzyloxycarbonyl-$N^2$-(tert-butyloxycarbonyl)-N-(2-ethoxycarbonylethyl)-L-arginamide.

The material was added to 30 ml of formic acid and was allowed to stand overnight. The formic acid was removed by distillation under reduced pressure, and the residue was washed with ethyl ether. Thus $N^G$, $N^G$-dibenzyloxycarbonyl-N-(2-ethoxycarbonylethyl)-L-argininamide formate was obtained.

To a mixture of 2.7 gram of the thus obtained $N^G,N^G$-dibenzyloxycarbonyl-N-(2-ethoxycarbonylethyl)-L-argininamide formate, 30 ml of dichloromethane and 0.6 g of triethylamine was added 1.6 g of dansyl chloride with stirring and cooling in an ice-bath. After stirring at 0° C. for 2 hours, 20 ml of water was added to the reaction mixture. After separation of the aqueous layer, the dichloromethane solution was dried over anhydrous Na$_2$SO$_4$. The Na$_2$SO$_4$ was removed by filtration and the solvent was removed by distillation to give a viscous oily product. The product was washed well with ethyl ether and purified by reprecipitation from a dichloromethane-petroleum ether mixture. N$^G$,N$^G$-dibenzyloxycarbonyl-N$^2$-dansyl-N-(2-ethoxycarbonyl-ethyl)-L-argininamide was obtained in powder form in 92% yield (based don N$^G$,N$^G$-dibenzyloxycarbonyl-N-(2-ethoxycarbonyl-ethyl)-L-argininamide formate).

| Elemental analysis (as C$_{39}$H$_{46}$N$_6$O$_9$S) | | | |
|---|---|---|---|
|  | C | H | N |
| Calculated: | 60.45 | 5.98 | 10.85 |
| Found: | 60.09 | 5.69 | 10.78 |

A 0.77 g amount of the thus obtained N$^G$, N$^G$-dibenzyloxycarbonyl-N$^2$-dansyl-N-(2-ethoxycarbonylethyl)-L-argininamide was dissolved in a mixture of 50 ml of ethanol and 5 ml of acetic acid. A 50 mg amount of palladium black was added to the mixture, which was then shaken in a stream of hydrogen for 48 hours at room temperature. After filtering off the catalyst, the filtrate was evaporated to give a viscous oily product. The product was purified as in Example 31 and N$^2$-dansyl-N-(2-ethoxycarbonylethyl)-L-argininamide diacetate was quantitatively obtained.

| Elemental analysis (as C$_{23}$H$_{34}$O$_4$N$_6$S.2CH$_3$COOH) | | | |
|---|---|---|---|
|  | C | H | N |
| Calculated: | 51.75 | 6.76 | 13.41 |
| Found: | 51.58 | 6.83 | 13.56 |

EXAMPLE 29

A 1.0 gram amount of N$^G$-nitro-N$^2$-dansyl-N-(n-butyl)-L-argininamide, which was preparred in the same manner as described in Example 26, was dissolved in a mixture of 1 ml of anisole and 2 ml of hydrogen fluoride, and the mixture was stirred for 30 minutes in an ice-bath. The hydrogen fluoride was evaporated in vacuo to afford an oily product, which was washed well with 100 ml of dry ethyl ether to remove the hydrogen fluoride. The thus obtained powdery product was neutralized with a solution of 3 ml of triethylamine in a small amount of water. Then N$^2$-dansyl-N-(n-butyl)-L-argininamide monohydrate was obtained in 73% yield; mp. 145°–148° C.

| Elemental analysis (as C$_{22}$H$_{34}$O$_3$N$_6$S.H$_2$O) | | | |
|---|---|---|---|
|  | C | H | N |
| Calculated: | 54.98 | 7.55 | 17.49 |
| Found: | 54.87 | 7.38 | 17.21 |

EXAMPLE 30

To 3.0 gram of N$^G$-nitro-N$^2$-dansyl-N-(2-phenylcarbamoylethyl)-L-argininamide, which was prepared in the same manner as described in Example 26, was added 3 ml of hydrogen fluoride at −80° C., and the mixture was stirred for 30 minutes in an ice-bath. The hydrogen fluoride was evaporated in vacuo to afford an oily product, which was washed well with 100 ml of dry ethyl ether to remove the hydrogen fluoride. The thus obtained oily product was dissolved in a small amount of alcohol and neutralized with 2 ml of triethylamine. The residue obtained by distilling off the alcohol was washed with water, and dissolved in ethyl acetate. The solution was dried over anhydrous Na$_2$SO$_4$, and the residue obtained by distilling off the ethyl acetate was dissolved in a small amount of acetic acid. The residue obtained after distilling the acetic acid was washed with dry ethyl ether, and N$^2$-dansyl-N-(2-phenylcarbamoylethyl)-L-argininamide diacetate was obtained in powder form in 77% yield.

| Elemental analysis (as C$_{27}$H$_{35}$O$_4$N$_7$S.2CH$_3$COOH) | | | |
|---|---|---|---|
|  | C | H | N |
| Calculated: | 55.26 | 6.43 | 14.56 |
| Found: | 54.98 | 6.26 | 14.39 |

EXAMPLE 31

A 2.68 gram amount of N$^G$-nitro-N$^2$-dansyl-N-(2-ethoxycarbonylmethyl)-L-argininamide, which was prepared in the same manner as described in Example 26, was dissolved in a mixture of 50 ml of ethanol and 5 ml of acetic acid.

A 50 mg amount of palladium black was added and the mixture was shaken in a stream of hydrogen for 100 hours at room temperature. After removal of the catalyst, the solvent was evaporated to obtain a viscous oily residue. Reprecipitation from ethanol-ethyl ether quantitatively gave N$^2$-dansyl-N-(2-ethoxycarbonylmethyl)-L-argininamide diacetate in powder form.

| Elemental analysis (as C$_{22}$H$_{32}$C$_5$N$_6$S.2CH$_3$COOH) | | | |
|---|---|---|---|
|  | C | H | N |
| Calculated: | 50.97 | 6.58 | 13.72 |
| Found: | 50.68 | 6.35 | 14.01 |

EXAMPLE 32

A 1.0 gram amount of N$^G$,N$^G$-dibenzyloxycarbonyl-N$^2$-dansyl-N-methoxyethyl-L-argininamide, which was prepared in the same manner as described in Example 28, was dissolved in a mixture of 25 ml of ethanol and 5 ml of acetic acid.

A 50 mg amount of 10% palladium black was added and the mixture was shaken in a stream of hydrogen for 10 hours at room temperature. After removal of the catalyst, the solvent was evaporated to obtain a viscous oily residue. To the residue about 15 ml of water and 3 ml of triethylamine were added, and the mixture was allowed to stand under cooling. N$^2$-dansyl-N-methoxyethyl-L-argininamide dihydrate was obtained in 93% yield; m.p. 130°–135° C.

| Elemental analysis (as C$_{21}$H$_{32}$O$_7$N$_6$S.2H$_2$O) | | | |
|---|---|---|---|
|  | C | H | N |
| Calculated: | 50.38 | 7.25 | 16.79 |
| Found: | 50.69 | 6.95 | 16.99 |

EXAMPLE 33

A 3.0 gram amount of 1-(N$^G$-nitro-N$^2$-dansyl-L-arginyl)piperidine, which was prepared in the same manner as described in Example 26, was dissolved in a mixture of 50 ml of ethanol and 5 ml of acetic acid.

A 50 mg amount of palladium black was added and the mixture was shaken in a stream of hydrogen for 120 hours at room temperature. After removal of the catalyst, the solvent was evaporated to give a viscous oily residue.

Reprecipitation from methanol-ethyl ether gave 1-($N^2$-dansyl-L-arginyl)piperidine diacetate in powder form in 70% yield.

| Elemental analysis (as $C_{23}H_{34}O_3N_6S.2CH_3COOH$) | | | |
|---|---|---|---|
| | C | H | N |
| Calculated: | 54.53 | 7.12 | 14.13 |
| Found: | 54.31 | 7.11 | 14.13 |

EXAMPLE 34

A 3.0 gram amount of 4-methyl-1-($N^G$,$N^G$-dibenzyloxycarbonyl-$N^2$-dansyl-L-arginyl)piperidine, which was prepared in the same manner as described in Example 28, was dissolved in a mixture of 50 ml of ethanol and 5 ml of acetic acid.

A 50 mg amount of palladium black was added and the mixture was shaken in a stream of hydrogen for 10 hours at room temperature. After removal of the catalyst, the solvent was evaporated to give a viscous oily residue.

Reprecipitation from methanol-ethyl ether gave 4-methyl-1-($N^2$-dansyl-L-arginyl)piperidine diacetate in powder form in 80% yield.

| Elemental analysis (as $C_{24}H_{36}O_3N_6S.2CH_3COOH$) | | | |
|---|---|---|---|
| | C | H | N |
| Calculated: | 55.24 | 7.29 | 13.81 |
| Found: | 55.01 | 7.49 | 14.00 |

EXAMPLE 35

To 2.0 grams of 1-($N^G$-nitro-$N^2$-dansyl-L-arginyl)-pyrrolidine, which was prepared in the same manner as described in Example 26, was added 2 ml of hydrogen fluoride at −80° C., and the mixture was stirred for 1 hour in an ice-bath. The hydrogen fluoride was evaporated in vacuo to afford an oily product, which was washed well with 100 ml of dry ethyl ether to remove the hydrogen fluoride. The ether was removed by decantation and the obtained oily product was dissolved in a small amount of water and neutralized with triethylamine. An oily product deposited which was collected and dissolved in ethanol containing 10% acetic acid. Ethyl ether was added to the solution to reprecipitate the product, 1-($N^2$-dansyl-L-arginyl)pyrrolidine diacetate, in 65% yield.

| Elemental analysis (as $C_{22}H_{32}O_3N_6S.2CH_3COOH$) | | | |
|---|---|---|---|
| | C | H | N |
| Calculated: | 53.77 | 6.94 | 14.47 |
| Found: | 52.58 | 7.16 | 14.21 |

EXAMPLE 36

A 0.5 g amount of 4 acetyl-1-($N^G$-nitro-$N^2$-dansyl-L-arginyl)piperidine, which was prepared in the same manner as described in Example 26, was dissolved in a mixture of 0.39 g of anisole and 2 ml of hydrogen fluoride at −80° C., and the mixture was stirred for 30 minutes in an ice-bath. The hydrogen fluoride was evaporated in vacuo to afford an oily product, which was washed well with 100 ml of dry ethyl ether to remove the hydrogen fluoride. The ether layer was removed by decantation, and the thus obtained oily product was dissolved in methanol. To the solution was added ethyl ether to reprecipitate the product, 4-acetyl-1-($N^2$-dansyl-L-arginyl)piperidine dihydrofluoride, in 72% yield.

| Elemental analysis (as $C_{25}H_{36}O_4N_6S.2HF$) | | | |
|---|---|---|---|
| | C | H | N |
| Calculated: | 53.94 | 6.88 | 15.10 |
| Found: | 53.80 | 6.80 | 14.92 |

Various other $N^2$-dansyl-L-argininamides or acid addition salts thereof were synthesized in accordance with the procedures of the above examples, and the test results are summarized in Table 1.

TABLE 1

Compound:

$$\text{NH}_2\text{-C(=NH)-NH-(CH}_2)_3\text{CHCOR}$$
with NHSO$_2$-(dansyl group with N(CH$_3)_2$)

| Sample No. | R | Addition moiety | Concentration required to prolong the coagulation time by a factor of 2 (μM) | Preparation process (Ex. No.) | m.p. (°C.) | Elemental analysis Upper: Calculated Lower: Found | | |
|---|---|---|---|---|---|---|---|---|
| | | | | | | C | H | N |
| 1 | —OCH$_3$ | 2HCl.H$_2$O | 30 | 1 and 12 | 147–150 | 44.62 | 6.11 | 13.69 |
| | | | | | | 44.42 | 6.17 | 13.64 |
| 2 | —OC$_2$H$_5$ | 2HCl | 8 | 2 | 140–144 | 47.24 | 6.15 | 13.77 |
| | | | | | | 46.95 | 6.21 | 14.60 |
| 3 | —O—n-C$_3$H$_7$ | 2HCl | 2 | 12 | ≧120 | 48.27 | 6.37 | 13.40 |
| | | | | | | 48.50 | 6.21 | 13.18 |
| 4 | —OCH(CH$_3$)$_2$ | 2HCl | 30 | 5 | 110–120 | 48.27 | 6.37 | 13.40 |
| | | | | | | 47.90 | 6.08 | 13.21 |
| 5 | —O—n-C$_4$H$_9$ | 2TsOH | 2 | 7 and 13 | 160–164 | 53.51 | 6.11 | 8.67 |
| | | | | | | 53.32 | 6.14 | 8.93 |
| 6 | —OCH$_2$CH(CH$_3$)$_2$ | 2TsOH | 110 | 9 | 146–151 | 53.51 | 6.11 | 8.67 |
| | | | | | | 53.54 | 6.11 | 8.65 |
| 7 | —O—n-C$_5$H$_{11}$ | 2TsOH | 5 | 8 | 164–169 | 54.06 | 6.25 | 8.52 |
| | | | | | | 53.86 | 6.10 | 8.53 |

TABLE 1-continued

Compound: guanidino-(CH₂)₃-CH(NHSO₂-dansyl)-COR

| Sample No. | R | Addition moiety | Concentration required to prolong the coagulation time by a factor of 2 (μM) | Preparation process (Ex. No.) | m.p. (°C.) | Elemental analysis Upper: Calculated Lower: Found C | H | N |
|---|---|---|---|---|---|---|---|---|
| 8 | —OCH₂CH₂CH(CH₃)₂ | 2TsOH | 10 | 10 | 163–168 | 54.06 / 53.74 | 6.25 / 6.09 | 8.52 / 8.57 |
| 9 | —O—n-C₆H₁₃ | 2TsOH | 8 | 6 | 190–193 | 54.59 / 54.33 | 6.39 / 6.48 | 8.38 / 8.11 |
| 10 | —O—CH₂CH(C₂H₅)(CH₂)₃CH₃ | 2TsOH | 50 | 4 | 170–174 | 55.60 / 55.37 | 6.65 / 6.59 | 8.11 / 8.18 |
| 11 | —O—CH₂—C₆H₅ | 2TsOH | 2 | 3 | 150–153 | 55.63 / 55.33 | 5.63 / 5.61 | 8.32 / 8.19 |
| 12 | —O—CH₂CH=CHCH₃ | 2TsOH | 2 | 11 | 148–153 | 53.64 / 53.64 | 5.88 / 5.90 | 8.69 / 8.35 |
| 13 | —O—CH₂CH₂C≡CH | 2TsOH | 4 | 11 | 133–143 | 53.78 / 53.51 | 5.64 / 5.52 | 8.71 / 8.78 |
| 14 | —O—cyclohexyl | 2TsOH | 60 | 11 | 177–182 | 54.72 / 54.33 | 6.16 / 6.18 | 8.40 / 8.17 |
| 15 | —O—CH₂—(tetrahydrofuran-2-yl) | 2TsOH | 20 | 11 | 144–150 | 53.15 / 52.57 | 5.91 / 5.89 | 8.38 / 8.30 |
| 16 | —O—CH₂CH₂OCH₃ | 2TsOH | 5 | 11 | 171.5–173 | 51.90 / 51.40 | 5.85 / 5.77 | 8.65 / 8.25 |
| 17 | —O—CH₂CH₂CH₂Cl | 2TsOH | 4 | 11 | 140–145 | 50.74 / 50.30 | 5.60 / 5.50 | 8.45 / 8.01 |
| 18 | —O—CH₂CH₂CH₂CH₂Cl | 2TsOH | 7 | 11 | 177–194 | 51.75 / 51.95 | 5.70 / 5.81 | 8.56 / 8.47 |
| 19 | —O—CH₂CH(NO₂)CH₂CH₃ | 2TsOH | 200 | 11 | 155–163 | 50.69 / 51.04 | 5.67 / 5.85 | 9.85 / 9.58 |
| 20 | —N(H)(C₂H₅) | H₂O | 100 | 18 | 220–222 | 53.08 / 53.34 | 7.13 / 7.18 | 18.57 / 18.86 |
| 21 | —N(H)(n-C₃H₇) | H₂O | 15 | 15 | 146–150 | 54.06 / 53.82 | 7.35 / 7.45 | 18.02 / 18.13 |
| 22 | —N(H)(n-C₄H₉) | H₂O | 25 | 14 and 29 | 145–148 | 54.98 / 54.72 | 7.55 / 7.61 | 17.49 / 17.25 |
| 23 | —N(H)(n-C₅H₁₁) | H₂O | 125 | 29 | 140–143 | 55.85 / 56.10 | 7.74 / 7.52 | 16.99 / 17.29 |

TABLE 1-continued

Compound:

$$\text{H}_2\text{N-C(=NH)-NH-(CH}_2)_3\text{-CH(NHSO}_2\text{-Ar)-COR}$$

where Ar = 5-(dimethylamino)naphthalen-1-yl

| Sample No. | R | Addition moiety | Concentration required to prolong the coagulation time by a factor of 2 (μM) | Preparation process (Ex. No.) | m.p. (°C.) | Elemental analysis Upper: Calculated Lower: Found C | H | N |
|---|---|---|---|---|---|---|---|---|
| 24 | −N(H)(n-C$_6$H$_{13}$) | H$_2$O | 20 | 19 | 130–135 | 56.67 / 56.38 | 7.93 / 7.59 | 16.53 / 16.34 |
| 25 | −N(H)(n-C$_7$H$_{15}$) | H$_2$O | 100 | 20 | 240–243 | 59.50 / 59.50 | 7.99 / 7.90 | 16.66 / 16.68 |
| 26 | −N(H)(CH(CH$_3$)$_2$) | — | 1000 | 16 | 218–221 | 56.23 / 56.38 | 7.19 / 7.20 | 18.74 / 18.94 |
| 27 | −N(H)(CH$_2$CH(CH$_3$)$_2$) | — | 100 | 21 | 155–160 | 57.12 / 56.82 | 7.41 / 7.41 | 18.17 / 17.90 |
| 28 | −N(H)(CH$_2$CH$_2$OCH$_3$) | 2H$_2$O | 4 | 22, 24 and 32 | 130–135 | 50.38 / 50.03 | 7.25 / 6.95 | 16.79 / 16.99 |
| 29 | −N(H)(CH$_2$CH$_2$CH$_2$OCH$_3$) | — | 65 | 32 | powder | 55.32 / 55.00 | 6.96 / 7.10 | 17.60 / 17.96 |
| 30 | −N(H)(CH$_2$CH$_2$OC$_2$H$_5$) | — | 5 | 26 | 230–232 | 55.32 / 55.34 | 6.96 / 7.16 | 17.60 / 17.69 |
| 31 | −N(H)(CH$_2$CO$_2$C$_2$H$_5$) | 2CH$_3$CO$_2$H | 160 | 31 | powder | 50.97 / 50.68 | 6.58 / 6.35 | 13.72 / 14.01 |
| 32 | −N(H)(CH$_2$CH$_2$CO$_2$CH$_3$) | 2HCl | 22 | 31 | powder | 46.72 / 46.58 | 5.70 / 5.91 | 14.86 / 14.97 |
| 33 | −N(H)(CH$_2$CH$_2$CO$_2$C$_2$H$_5$) | 2CH$_3$CO$_2$H | 5 | 28 | powder | 51.75 / 51.58 | 6.76 / 6.83 | 13.41 / 13.56 |
| 34 | −N(H)(CH$_2$CH$_2$CH$_2$CO$_2$C$_2$H$_5$) | 2CH$_3$CO$_2$H | 500 | 31 | powder | 52.49 / 52.51 | 6.92 / 7.13 | 13.12 / 13.01 |
| 35 | −N(H)(CH$_2$CH=CH$_2$) | H$_2$O | 10 | 32 | 140–145 | 54.29 / 53.92 | 6.94 / 6.88 | 18.09 / 18.09 |

TABLE 1-continued

Compound $$\text{H}_2\text{N-C(=NH)-NH-(CH}_2)_3\text{-CH(NHSO}_2\text{-Naphthyl-N(CH}_3)_2)\text{-COR}$$

| Sample No. | R | Addition moiety | Concentration required to prolong the coagulation time by a factor of 2 (μM) | Preparation process (Ex. No.) | m.p. (°C.) | Elemental analysis Upper: Calculated Lower: Found | | |
|---|---|---|---|---|---|---|---|---|
| | | | | | | C | H | N |
| 36 | −N(H)−CH(CH$_2$)(CH$_2$) (cyclopropyl) | 2H$_2$O | 200 | 32 | 165–168 | 52.26 52.00 | 7.10 7.10 | 17.42 17.53 |
| 37 | −N(H)−CH$_2$−cyclohexyl | — | 40 | 23 | 253–256 | 59.73 59.96 | 7.62 7.48 | 16.72 16.73 |
| 38 | −N(H)−C$_6$H$_5$ | 2CH$_3$CO$_2$H | 100 | 27 | powder | 55.80 55.90 | 6.36 6.48 | 13.95 14.15 |
| 39 | −N(H)−CH$_2$−phenyl | — | 50 | 29 | 244–246 | 60.46 59.97 | 6.50 6.46 | 16.92 16.77 |
| 40 | −N(H)−CH$_2$CH$_2$−phenyl | 2H$_2$O | 150 | 17 | 143–147 | 57.13 57.34 | 7.01 6.72 | 15.38 15.64 |
| 41 | −N(H)−CH$_2$CH$_2$CH$_2$−phenyl | H$_2$O | 27 | 26 | 131–135 | 59.75 59.39 | 7.06 6.98 | 15.49 15.23 |
| 42 | −N(H)−CH$_2$CH$_2$CONH−phenyl | 2CH$_3$CO$_2$H | >500 | 30 | powder | 55.26 54.98 | 6.43 6.26 | 14.56 14.39 |
| 43 | −N(H)−CH$_2$CON(pyrrolidine) | 2CH$_3$CO$_2$H | 370 | 31 | powder | 52.73 52.54 | 6.80 6.63 | 15.38 15.13 |
| 44 | −N(CH$_3$)−CH$_2$CH$_2$C(=O)CH$_3$ | 2HF | | 36 | powder | 52.26 52.02 | 6.48 6.48 | 15.90 15.81 |
| 45 | −N(C$_2$H$_5$)(C$_2$H$_5$) | 2CH$_3$CO$_2$H | 55 | 27 | powder | 53.59 53.99 | 7.27 7.30 | 14.42 14.82 |

TABLE 1-continued

Compound:

C(=NH)(NH₂)—NH—(CH₂)₃CH(NHSO₂-[5-(dimethylamino)naphthalen-1-yl])COR

| Sample No. | R | Addition moiety | Concentration required to prolong the coagulation time by a factor of 2 (μM) | Preparation process (Ex. No.) | m.p. (°C.) | Elemental analysis Upper: Calculated Lower: Found C | H | N |
|---|---|---|---|---|---|---|---|---|
| 46 | —N(n-C₄H₉)₂ | 2CH₃CO₂H | 39 | 27 | powder | 56.41 / 55.99 | 7.89 / 7.65 | 13.16 / 13.36 |
| 47 | —N(CH₃)(n-C₄H₉) | 2CH₃CO₂H | 2 | 26 | powder | 54.35 / 54.33 | 7.43 / 7.43 | 14.09 / 14.00 |
| 48 | —N(C₂H₅)(n-C₄H₉) | 2CH₃CO₂H | 50 | 27 | powder | 55.06 / 54.99 | 7.59 / 7.89 | 13.76 / 14.01 |
| 49 | —N(CH₃)(CH₂CO₂C₂H₅) | 2CH₃CO₂H | 59 | 31 | powder | 51.75 / 51.49 | 6.76 / 6.84 | 13.41 / 13.06 |
| 50 | —N(CH₃)(CH₂CH₂CO₂CH₃) | 2CH₃CO₂H | 2.5 | 31 | powder | 51.75 / 51.49 | 6.76 / 6.93 | 13.41 / 13.70 |
| 51 | —N(CH₃)(CH₂CH₂CO₂C₂H₅) | 2CH₃CO₂H | 15 | 31 | powder | 52.49 / 52.66 | 6.92 / 7.18 | 13.12 / 13.51 |
| 52 | —N(CH₃)(CH₂C₆H₅) | 2CH₃CO₂H | 7 | 27 | powder | 57.12 / 56.92 | 6.71 / 6.79 | 13.33 / 13.61 |
| 53 | pyrrolidin-1-yl | 2CH₃CO₂H | 3.3 | 35 | powder | 53.77 / 53.58 | 6.94 / 7.16 | 14.47 / 14.21 |
| 54 | 2-(ethoxycarbonyl)pyrrolidin-1-yl | 2CH₃CO₂H | 780 | 31 | powder | 53.36 / 53.39 | 6.79 / 7.05 | 12.88 / 12.70 |
| 55 | piperidin-1-yl | 2CH₃CO₂H | 0.9 | 25 and 33 | powder | 54.53 / 54.23 | 7.12 / 7.11 | 14.13 / 14.43 |
| 56 | 2-methylpiperidin-1-yl | 2CH₃CO₂H | 1.3 | 33 | powder | 55.24 / 55.01 | 7.29 / 7.50 | 13.81 / 14.09 |

TABLE 1-continued

Compound: C(=NH)(NH₂)–NH–(CH₂)₃–CH(NHSO₂–[5-dimethylamino-naphthalen-1-yl])–COR

| Sample No. | R | Addition moiety | Concentration required to prolong the coagulation time by a factor of 2 (μM) | Preparation process (Ex. No.) | m.p. (°C.) | Elemental analysis Upper: Calculated Lower: Found C | H | N |
|---|---|---|---|---|---|---|---|---|
| 57 | 3-methyl-piperidino | 2CH₃CO₂H | 6.5 | 33 | powder | 55.24 / 55.13 | 7.29 / 7.44 | 13.81 / 14.00 |
| 58 | 4-methyl-piperidino | 2CH₃CO₂H | 0.3 | 34 | powder | 55.24 / 55.01 | 7.29 / 7.49 | 13.81 / 14.00 |
| 59 | 4-ethyl-piperidino | 2CH₃CO₂H | 0.1 | 33 | powder | 55.93 / 55.87 | 7.45 / 7.66 | 13.50 / 13.81 |
| 60 | 4-n-propyl-piperidino | 2CH₃CO₂H | 1.0 | 33 | powder | 56.78 / 56.61 | 7.60 / 8.00 | 13.20 / 13.06 |
| 61 | 4-isopropyl-piperidino | 2CH₃CO₂H | 1.0 | 33 | powder | 56.78 / 56.48 | 7.60 / 7.64 | 13.20 / 13.10 |
| 62 | 4-methoxycarbonyl-piperidino | 2CH₃CO₂H | 2.8 | 31 | powder | 53.36 / 53.69 | 6.80 / 7.18 | 12.88 / 12.91 |
| 63 | 4-carbamoyl-piperidino | 2CH₃CO₂H | 100 | 31 | powder | 53.92 / 53.68 | 6.95 / 6.76 | 13.48 / 13.35 |
| 64 | hexamethyleneimino | 2CH₃CO₂H | 0.9 | 33 | powder | 55.24 / 55.49 | 7.29 / 7.38 | 13.81 / 14.11 |
| 65 | heptamethyleneimino | 2CH₃CO₂H | 1 | 33 | powder | 55.93 / 55.71 | 7.45 / 7.73 | 13.50 / 13.20 |
| 66 | octamethyleneimino | 2CH₃CO₂H | 2 | 33 | powder | 56.78 / 56.59 | 7.60 / 7.87 | 13.20 / 13.00 |

TABLE 1-continued

Compound:

$$\text{H}_2\text{N-C(=NH)-NH-(CH}_2)_3\text{CH(NHSO}_2\text{-Dansyl)COR}$$

where the sulfonyl is attached to naphthalene bearing 5-N(CH$_3$)$_2$

| Sample No. | R | Addition moiety | Concentration required to prolong the coagulation time by a factor of 2 (μM) | Preparation process (Ex. No.) | m.p. (°C.) | Elemental analysis Upper: Calculated Lower: Found C / H / N |
|---|---|---|---|---|---|---|
| 67 | morpholino (—N(CH$_2$CH$_2$)$_2$O) | 2CH$_3$CO$_2$H | 1.5 | 33 | powder | 52.33 6.76 14.09 / 52.53 7.00 14.39 |
| 68 | 2,6-dimethylmorpholino | 2CH$_3$CO$_2$H | 20 | 33 | powder | 53.83 7.10 13.45 / 53.55 7.17 13.81 |
| 69 | 3-azabicyclo[3.2.1]octyl | 2CH$_3$CO$_2$H | 10 | 33 | powder | 56.76 7.30 13.24 / 56.62 7.59 13.52 |
| 70 | isoindolin-2-yl | 2CH$_3$CO$_2$H | 0.67 | 33 | powder | 57.31 6.41 13.37 / 57.03 6.57 13.62 |
| 71 | 4-methylpiperazin-1-yl | 2CH$_3$CO$_2$H | 2 | 33 | powder | 53.18 7.11 16.08 / 53.01 7.00 15.79 |
| 72 | 1,2,3,4-tetrahydroquinolin-1-yl | 2CH$_3$CO$_2$H | 6.5 | 33 | powder | 57.92 6.59 13.08 / 57.71 6.58 12.97 |
| 73 | 3-acetylpiperidin-1-yl | 2HF | — | 36 | powder | 52.26 6.48 15.90 / 52.02 6.48 15.81 |

Having now fully described the invention, it will be apparent to one of ordinary skill in the art that many changes and modifications can be made thereto without departing from the spirit or scope of the invention as set forth herein.

What is claimed as new and intended to be covered by Letters Patent is:

1. N$^2$-Dansyl-L-Argininamides having the formula

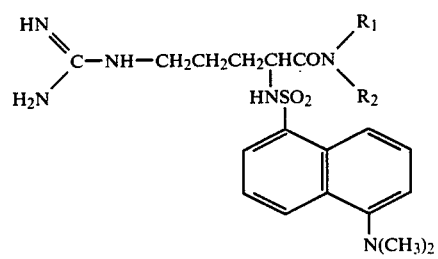

wherein R$_2$ is hydrogen or methyl and R$_1$ is —CH$_2$CO$_2$C$_2$H$_5$ or —CH$_2$CH$_2$CH$_2$CO$_2$C$_2$H$_5$.

2. The compound of claim 1, wherein
$R_2 = H$
$R_1 = -CH_2-CO_2C_2H_5$.
3. The compound of claim 1, wherein
$R_2 = H$
$R_1 = -CH_2-CH_2-CH_2-CO_2-C_2H_5$.
4. The compound of claim 1, wherein
$R_2 = CH_3$
$R_1 = -CH_2-CO_2C_2H_5$.

5. An antithrombotic composition which comprises an antithrombotically effective amount of a compound of claim 1 and a pharmaceutically acceptable carrier.

6. A method for inhibiting activity and suppressing activation of thrombin in vivo, which comprises administering to a patient a pharmaceutically effective amount of the composition according to claim 5.

* * * * *